(12) United States Patent
Bazargan et al.

(10) Patent No.: US 11,701,467 B2
(45) Date of Patent: Jul. 18, 2023

(54) METHODS AND DEVICES FOR OCCLUSION DETECTION USING ACTUATOR SENSORS

(71) Applicant: MEDTRONIC MINIMED, INC., Northridge, CA (US)

(72) Inventors: Afshin Bazargan, Simi Valley, CA (US); Adam S. Trock, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 531 days.

(21) Appl. No.: 16/776,081

(22) Filed: Jan. 29, 2020

(65) Prior Publication Data

US 2020/0246540 A1 Aug. 6, 2020

Related U.S. Application Data

(60) Provisional application No. 62/800,310, filed on Feb. 1, 2019.

(51) Int. Cl.
| | | |
|---|---|---|
| *A61M 5/168* | (2006.01) | |
| *A61M 5/145* | (2006.01) | |
| *A61M 5/142* | (2006.01) | |

(52) U.S. Cl.
CPC ...... *A61M 5/16831* (2013.01); *A61M 5/1452* (2013.01); *A61M 5/1458* (2013.01); *A61M 5/14244* (2013.01); *A61M 5/14566* (2013.01); *A61M 5/16804* (2013.01); *A61M 2005/14506* (2013.01); *A61M 2005/16863* (2013.01); *A61M 2005/16868* (2013.01); *A61M 2205/3331* (2013.01); *A61M 2205/3365* (2013.01); *A61M 2205/502* (2013.01); *A61M 2230/201* (2013.01)

(58) Field of Classification Search
CPC .... A61M 5/16831; A61M 2005/16863; A61M 5/1452; A61M 2005/14506; A61M 2205/3365; A61M 2205/502; A61M 5/14244; A61M 5/145; A61M 5/5086; A61M 2205/103; A61M 2205/10; A61M 2205/15; A61M 2205/8206; A61M 5/1458; A61M 5/16804; A61M 2005/06868; A61M 2005/16868; A61M 2005/16872
See application file for complete search history.

(56) References Cited

U.S. PATENT DOCUMENTS

| | | |
|---|---|---|
| 4,562,751 A | 1/1986 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |

(Continued)

*Primary Examiner* — Kevin C Sirmons
*Assistant Examiner* — Avery Smale
(74) *Attorney, Agent, or Firm* — Shumaker & Sieffert, P.A.

(57) ABSTRACT

Infusion devices, systems, and related operating methods are provided. A method of detecting an occlusion in a fluid path involves a control module of an infusion device operating a driver module to provide energy to an actuation arrangement to achieve a commanded actuation state, wherein the actuation arrangement is coupled to a plunger configured to deliver fluid via the fluid path, obtaining a measured actuation state of the actuation arrangement via a sensing arrangement, and detecting an occlusion condition based on a relationship between the commanded actuation state and the measured actuation state.

16 Claims, 10 Drawing Sheets

(56) References Cited

U.S. PATENT DOCUMENTS

| | | |
|---|---|---|
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,603,027 B2 | 12/2013 | Favreau |
| 8,674,288 B2 | 3/2014 | Hanson et al. |
| 9,402,949 B2 | 8/2016 | Tieck et al. |
| 2006/0031094 A1 | 2/2006 | Cohen et al. |
| 2006/0184154 A1* | 8/2006 | Moberg ............ A61M 5/16854 604/151 |
| 2007/0123819 A1 | 5/2007 | Mernoe et al. |
| 2010/0160861 A1 | 6/2010 | Causey, III et al. |
| 2013/0338630 A1 | 12/2013 | Agrawal et al. |
| 2014/0066889 A1 | 3/2014 | Grosman et al. |
| 2015/0025499 A1* | 1/2015 | Trock ................ A61M 5/16831 604/152 |
| 2018/0169334 A1 | 6/2018 | Grosman et al. |

* cited by examiner

| CONDITION | STROKE | MOTOR ON TIME (CAPTURED IN COUNTS) | COAST COUNTS | TOTAL COUNTS | ERROR | ON/COAST RATIO |
|---|---|---|---|---|---|---|
| NO OCCLUSION | 1 | 22 | 80 | 102 | | 0.28 |
| NO OCCLUSION | 2 | 19 | 79 | 98 | -2 | 0.24 |
| NO OCCLUSION | 3 | 20 | 80 | 100 | 0 | 0.25 |
| NO OCCLUSION | 4 | 20 | 78 | 98 | -2 | 0.26 |
| NO OCCLUSION | 5 | 21 | 78 | 99 | -1 | 0.27 |
| OCCLUSION | 6 | 22 | 75 | 97 | -3 | 0.29 |
| OCCLUSION | 7 | 25 | 70 | 95 | -5 | 0.36 |
| OCCLUSION | 8 | 30 | 60 | 90 | -10 | 0.50 |
| OCCLUSION | 9 | 35 | 50 | 85 | -15 | 0.70 |
| OCCLUSION | 10 | 40 | 45 | 85 | -15 | 0.89 |
| OCCLUSION | 11 | 45 | 35 | 80 | -20 | 1.29 |

METHODS AND DEVICES FOR OCCLUSION DETECTION USING ACTUATOR SENSORS

CROSS-REFERENCE TO RELATED APPLICATION(S)

This application claims the benefit of U.S. Provisional Patent Application Ser. No. 62/800,310, filed Feb. 1, 2019, the contents of which are incorporated by reference herein in its entirety.

TECHNICAL FIELD

Embodiments of the subject matter described herein relate generally to medical devices, and more particularly, embodiments of the subject matter relate to infusion devices and related occlusion detection methods that do not require force sensors or dedicated occlusion detection components.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Different infusion pump devices may have different form factors, constraints, or otherwise utilize different techniques, which may result in the particular type of actuator drive system varying from one type of infusion pump device to the next. Often, fluid infusion devices include a force sensor or some other sensing arrangement designed to detect and indicate potential non-delivery of medication to the patient due to a fluid path occlusion or some other condition within the infusion device. However, such additional components increase costs and introduce additional design concerns with respect to installing and packaging the sensor (e.g., where to place the sensor, where or how to run wiring to/from the sensor to enable communication with the sensor, ensuring the device housing includes sufficient space for the sensor, etc.). Accordingly, it is desirable to obviate the need for such components to reduce costs, form factor, device size, and the like without compromising safety or reliability. Other desirable features and characteristics will become apparent from the subsequent detailed description and the appended claims, taken in conjunction with the accompanying drawings and this background.

BRIEF SUMMARY

Electromechanical actuation devices, systems, and related methods suitable for use detecting anomalous conditions in medical devices or systems, such as an infusion device or infusion system, are provided. One exemplary method of detecting an anomalous condition with respect to a fluid path based on operation of an actuation arrangement configured to deliver fluid via the fluid path involves providing input power to the actuation arrangement to produce actuation of the actuation arrangement, identifying an active amount of actuation of the actuation arrangement concurrent to the input power being provided to the actuation arrangement, disabling the input power to the actuation arrangement, identifying a passive amount of actuation of the actuation arrangement after disabling the input power to the actuation arrangement, and detecting the anomalous condition based on a relationship between the active amount and the passive amount.

An exemplary infusion device is provided that includes an actuation arrangement coupled to a plunger to deliver fluid via a fluid path, a driver module coupled to the actuation arrangement to selectively provide input power to the actuation arrangement, a sensing arrangement to measure actuation of the actuation arrangement, and a control module coupled to the driver module and the sensing arrangement to operate the driver module to provide the input power to the actuation arrangement, identify an active amount of actuation of the actuation arrangement concurrent to the input power being provided to the actuation arrangement using the sensing arrangement, operate the driver module to disable the input power to the actuation arrangement, identify a passive amount of actuation of the actuation arrangement after disabling the input power to the actuation arrangement using the sensing arrangement, and detect an anomalous condition with respect to the fluid path based on a relationship between the active amount and the passive amount.

In one embodiment, an exemplary method of detecting an occlusion in a fluid path by a control module associated with an infusion device involves operating a driver module to provide current flow to a motor to produce a first amount of rotation of a rotor of the motor, wherein the rotor is coupled to a plunger configured to deliver fluid via the fluid path, identifying a second amount of rotation of the rotor after disabling the current flow to the motor using a rotor sensing arrangement, detecting an occlusion condition based on a relationship between the first amount and the second amount, and generating a user notification in response to detecting the occlusion condition.

In another embodiment, a method of detecting an occlusion in a fluid path involves a control module of an infusion device operating a driver module to provide energy to an actuation arrangement to achieve a commanded actuation state, wherein the actuation arrangement is coupled to a plunger configured to deliver fluid via the fluid path, obtaining a measured actuation state of the actuation arrangement via a sensing arrangement, and detecting an occlusion condition based on a relationship between the commanded actuation state and the measured actuation state.

Another embodiment of an infusion device includes an actuation arrangement coupled to a plunger to deliver fluid via a fluid path, a driver module coupled to the actuation arrangement to selectively provide input power to the actuation arrangement, a sensing arrangement to measure actuation of the actuation arrangement, and a control module coupled to the driver module and the sensing arrangement to operate the driver module to provide the input power to the actuation arrangement to achieve a commanded actuation state, obtain a measured actuation state of the actuation arrangement using the sensing arrangement, and detect an anomalous condition based on a relationship between the commanded actuation state and the measured actuation state.

Another embodiment of a method of detecting an occlusion in a fluid path associated with an infusion device including a motor having a rotor coupled to a plunger displaceable to deliver fluid via the fluid path involves a control module of the infusion device operating a driver module to provide current flow to the motor to achieve a commanded rotation of the rotor, obtaining a measured rotor position via a rotor sensing arrangement, detecting an occlusion condition based at least in part on the measured rotor position, and initiating a remedial action in response to detecting the occlusion condition.

In yet another embodiment, a method of detecting an anomalous condition with respect to a fluid path involves providing energy to an actuation arrangement to produce actuation, wherein the actuation arrangement is coupled to a plunger configured to deliver fluid via the fluid path, monitoring an orientation of the actuation arrangement using a sensing arrangement, and detecting an anomalous condition based on the orientation of the actuation arrangement.

In yet another embodiment, an infusion device includes a motor comprising a rotor coupled to a drive system operable to displace a plunger to deliver fluid via a fluid path, a sensing arrangement to provide one or more measurement outputs influenced by an orientation of a rotational axis of the rotor with respect to a reference axis, and a control module coupled to the sensing arrangement to determine the orientation of the rotational axis based at least in part on the one or more measurement outputs and detect an anomalous condition with respect to the fluid path based on a difference between the rotational axis and the reference axis.

Another exemplary method of detecting an occlusion in a fluid path associated with an infusion device including a motor having a rotor coupled to a drive system operable to displace a plunger to deliver fluid via the fluid path involves a control module of the infusion device operating a driver module coupled to the motor to enable current flow to the motor, obtaining measurement output from a sensing arrangement, wherein the measurement output is influenced by an orientation of the rotor with respect to a reference rotational axis, determining a difference between a rotational axis of the rotor and the reference rotational axis based on the measurement output, detecting an occlusion condition with respect to the fluid path when the difference is greater than an occlusion detection threshold, and initiating a remedial action in response to detecting the occlusion condition.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
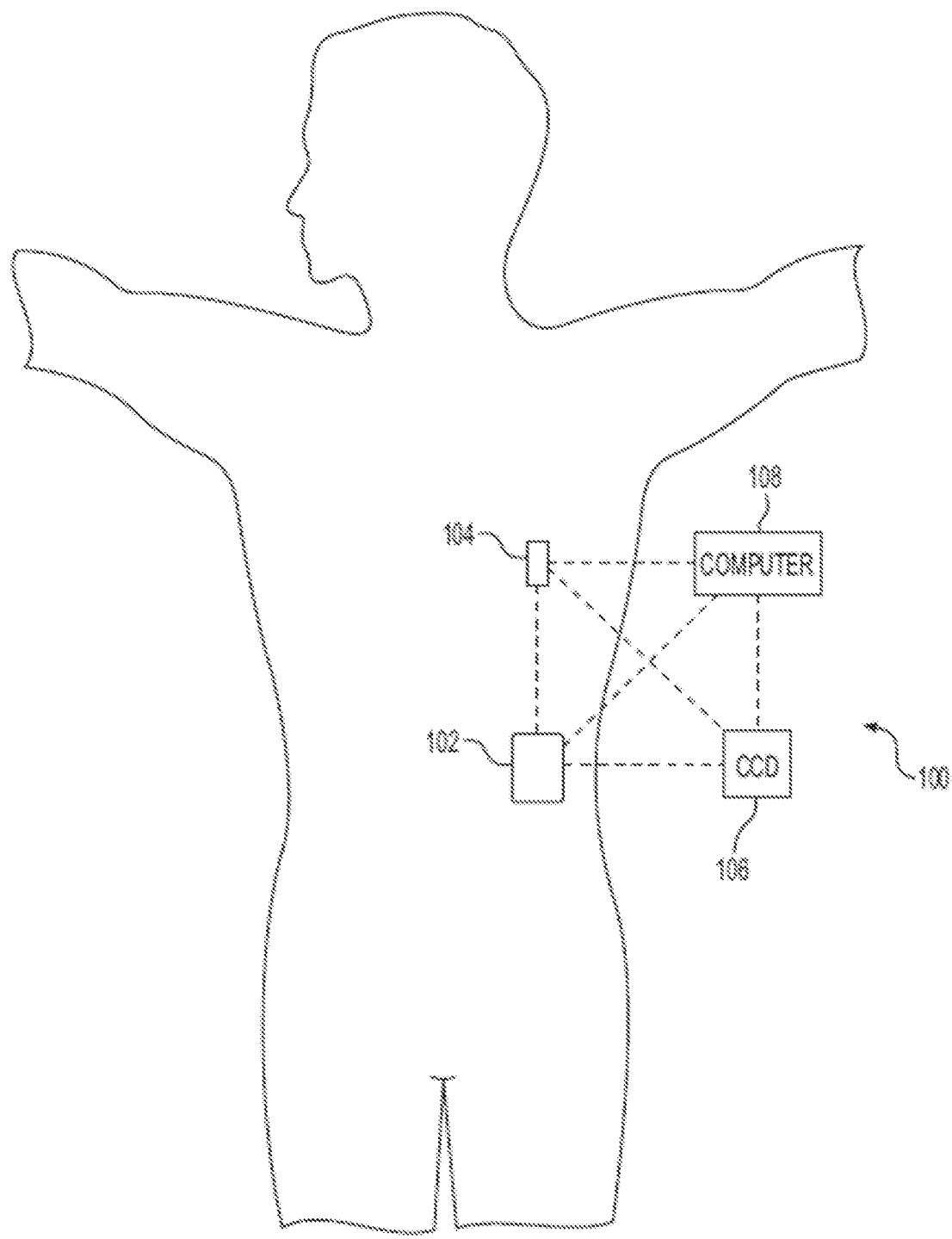
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes an electromechanical actuator, exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of other medical devices, such as injection pens (e.g., smart injection pens) and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to displace a plunger (or stopper) or other delivery mechanism to deliver a dosage of fluid, such as insulin, from a reservoir provided within the fluid infusion device to the body of a patient. Dosage commands that govern actuation may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below primarily in the context of FIGS. 3-12, exemplary embodiments described herein are capable of detecting an occlusion condition in a fluid path without reliance on a force sensor, volume sensor, or other sensing arrangement(s) that are dedicated to detecting occlusion. In this regard, the subject matter described herein utilizes motor or actuator dynamics, motor or actuator position sensors, or other data or information pertaining to operation of the motor or actuator to detect an occlusion condition. As used herein, an occlusion condition should be understood as referring to a condition in which delivery of fluid along a fluid path is impaired by an obstruction or impediment along the fluid path. While the subject matter is described herein primarily in the context of an occlusion condition for purposes of explanation, it will be appreciated that the subject matter could be implemented in an equivalent manner for a leakage condition (e.g., a condition in which delivery of fluid along a fluid path is impaired by a loss of fluid (or pressure) caused by a degraded seal or a leak in a fluid reservoir or elsewhere along the fluid path) or another anomalous condition with respect to fluid delivery or a drive system associated therewith (e.g., jammed, slipped or stripped gears, or other drive train anomalies). Accordingly, the subject matter described herein is not necessarily limited to implementation in the context of occlusion conditions.

Infusion System Overview

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
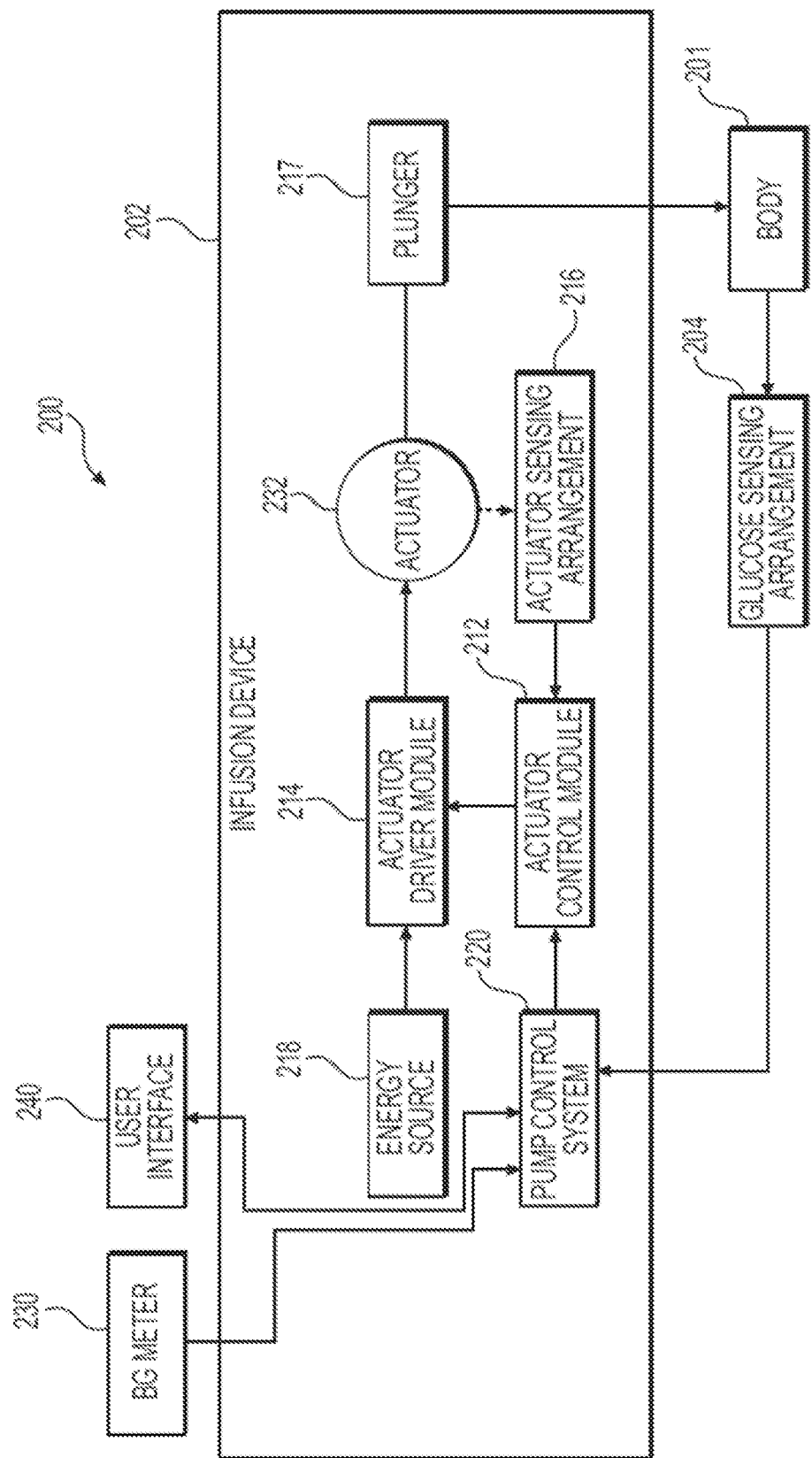
FIG. 2 is a block diagram of an exemplary control system suitable for use with a fluid infusion device in one or more embodiments.

FIG. 2 depicts an exemplary embodiment of a control system 200 suitable for use with an infusion device 202, such as the infusion device 102 described above. The control system 200 is capable of controlling or otherwise regulating a physiological condition in the body 201 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 204 (e.g., sensing arrangement 104) communicatively coupled to the infusion device 202. However, it should be noted that in alternative embodiments, the condition being regulated by the control system 200 may be correlative to the measured values obtained by the sensing arrangement 204. That said, for clarity and purposes of explanation, the subject matter may be described herein in the context of the sensing arrangement 204 being realized as a glucose sensing arrangement that senses, detects, measures or otherwise quantifies the patient's glucose level, which is being regulated in the body 201 of the patient by the control system 200.

In exemplary embodiments, the sensing arrangement 204 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 201 of the patient. The output electrical signals are filtered or otherwise processed to obtain a measurement value indicative of the patient's interstitial fluid glucose level. In some embodiments, a blood glucose meter 230, such as a finger stick device, is utilized to directly sense, detect, measure or otherwise quantify the blood glucose in the body 201 of the patient. In this regard, the blood glucose meter 230 outputs or otherwise provides a measured blood glucose value that may be utilized as a reference measurement for calibrating the sensing arrangement 204 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 204 may alternatively be referred to herein as the sensor glucose value, the sensed glucose value, or variants thereof.

Although not illustrated in FIG. 2, practical embodiments of the control system 200 may include one or more additional sensing arrangements configured to sense, detect, measure or otherwise quantify a characteristic of the body of the patient that is indicative of a condition in the body of the patient. For example, in addition to the glucose sensing arrangement 204, one or more auxiliary sensing arrangements may be worn, carried, or otherwise associated with the body 201 of the patient to measure characteristics or conditions that may influence the patient's glucose levels or insulin sensitivity, such as a heart rate sensor (or monitor), a lactate sensor, a ketone sensor, an acceleration sensor (or accelerometer), an environmental sensor, and/or the like.

In the illustrated embodiment, the pump control system 220 generally represents the electronics and other components of the infusion device 202 that control operation of the fluid infusion device 202 according to a desired infusion delivery program in a manner that is influenced by the sensed glucose value indicating the current glucose level in the body 201 of the patient. For example, to support a closed-loop operating mode, the pump control system 220 maintains, receives, or otherwise obtains a target or commanded glucose value, and automatically generates or otherwise determines dosage commands for operating an electromechanical actuator 232 (e.g., a BLDC motor, a BDC motor, a stepper motor, a shape-memory alloy actuators, or the like) to displace the plunger 217 and deliver insulin to the body 201 of the patient based on the difference between the sensed glucose value and the target glucose value. In other operating modes, the pump control system 220 may generate or otherwise determine dosage commands configured to maintain the sensed glucose value below an upper glucose limit, above a lower glucose limit, or otherwise within a desired range of glucose values. In practice, the infusion device 202 may store or otherwise maintain the target value, upper and/or lower glucose limit(s), insulin delivery limit(s), and/or other glucose threshold value(s) in a data storage element accessible to the pump control system 220. As described in greater detail, in one or more exemplary embodiments, the pump control system 220 automatically adjusts or adapts one or more parameters or other control information used to generate commands for operating the electromechanical actuator 232 in a manner that accounts for a likely change in the patient's glucose level or insulin response resulting from a meal, exercise, or other activity.

Still referring to FIG. 2, the target glucose value and other threshold glucose values utilized by the pump control system 220 may be received from an external component (e.g., CCD 106 and/or computing device 108) or be input by a patient via a user interface element 240 associated with the infusion device 202. In practice, the one or more user interface element(s) 240 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 240 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 2 depicts the user interface element(s) 240 as being separate from the infusion device 202, in practice, one or more of the user interface element(s) 240 may be integrated with the infusion device 202. Furthermore, in some embodiments, one or more user interface element(s) 240 are integrated with the sensing arrangement 204 in addition to and/or in alternative to the user interface element(s) 240 integrated with the infusion device 202. The user interface element(s) 240 may be manipulated by the patient to operate the infusion device 202 to deliver correction boluses, adjust target and/or threshold values, modify the delivery control scheme or operating mode, and the like, as desired.

Still referring to FIG. 2, in the illustrated embodiment, the infusion device 202 includes an actuator control module 212 coupled to an electromechanical actuator driver module 214, which, in turn, is coupled to the electromechanical actuator 232 that is operable to displace a plunger 217 in a reservoir and provide a desired amount of fluid to the body 201 of a patient. In this regard, displacement of the plunger 217 results in the delivery of a fluid, such as insulin, that is capable of influencing the patient's physiological condition to the body 201 of the patient via a fluid delivery path (e.g., via tubing of an infusion set). The electromechanical actuator driver module 214 is coupled between an energy source 218 and the electromechanical actuator 232, and the actuator control module 212 generates or otherwise provides command signals that operate the electromechanical actuator driver module 214 to provide current (or power) from the energy source 218 to the electromechanical actuator 232 to displace the plunger 217 in response to receiving, from a pump control system 220, a dosage command indicative of the desired amount of fluid to be delivered. It should be noted that FIG. 2 is a simplified representation for purposes of explanation, and it will be appreciated that, in practice, the actuator 232 may be a component of an actuation arrangement or system that includes gears and/or other drive train components that convert rotational motion (e.g., by a rotor of an electric motor) to a translational displacement of the plunger 217.

In exemplary embodiments, the energy source 218 is realized as a battery housed within the infusion device 202 that provides direct current (DC) power. In this regard, the electromechanical actuator driver module 214 generally represents the combination of logic circuitry, hardware and/or other electrical components configured to convert or otherwise transfer DC power provided by the energy source 218 into alternating electrical signals applied to inputs of the electromechanical actuator 232 (e.g., respective phases of the stator windings of a motor) that result in current flow that causes the electromechanical actuator 232 to displace the plunger 217. For example, the actuator driver module 214 may generate voltage signals applied to the phases of stator windings of a motor that result in current flow through the stator windings that generates a stator magnetic field and causes a rotor of the motor to rotate.

The actuator control module 212 is configured to receive or otherwise obtain a commanded dosage from the pump control system 220, convert the commanded dosage to a commanded translational displacement of the plunger 217, and command, signal, or otherwise operate the electromechanical actuator driver module 214 to cause actuation of the electromechanical actuator 232 by an amount that produces the commanded translational displacement of the plunger 217. For example, when the actuator 232 is realized as a motor, the actuator control module 212 may determine an amount of rotation of the rotor required to produce translational displacement of the plunger 217 that achieves the commanded dosage received from the pump control system 220. The actuator control module 212 monitors the current actuation state indicated by the output of a sensing arrangement 216 (e.g., the rotational position (or orientation) of the rotor with respect to the stator of a motor that is indicated by a rotor sensing arrangement) and provides one or more command signals to the actuator driver module 214 until achieving the desired amount of actuation, and thereby the desired delivery of fluid to the patient. As described in greater detail below, in some embodiments, the actuator control module 212 may operate the actuator 232 to deliver a dosage command using a series or sequences of drive cycles to that provide a corresponding series or sequences of smaller dosages that cumulatively equal the commanded dosage. For example, a commanded dosage of 20 microliters (μL) may be achieved via operating the actuator 232 through a series of forty drive cycles, where each drive cycle provides a 0.5 μL dosage.

Depending on the embodiment, the actuator control module 212 may be implemented or realized with a general purpose processor, a microprocessor, a controller, a microcontroller, a state machine, a content addressable memory, an application specific integrated circuit, a field programmable gate array, any suitable programmable logic device, discrete or transistor logic, discrete hardware components, or any combination thereof, designed to perform the functions described herein. In exemplary embodiments, the actuator control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the actuator control module 212. The computer-executable programming instructions, when read and executed by the actuator control module 212, cause the actuator control module 212 to perform or otherwise support the tasks, operations, functions, and processes described herein.

It should be appreciated that FIG. 2 is a simplified representation of the infusion device 202 for purposes of explanation and is not intended to limit the subject matter described herein in any way. In this regard, depending on the embodiment, some features and/or functionality of the sensing arrangement 204 may implemented by or otherwise integrated into the pump control system 220, or vice versa. Similarly, in practice, the features and/or functionality of the actuator control module 212 may implemented by or otherwise integrated into the pump control system 220, or vice versa. Furthermore, the features and/or functionality of the pump control system 220 may be implemented by control electronics located in the fluid infusion device 202, while in alternative embodiments, the pump control system 220 may be implemented by a remote computing device that is physically distinct and/or separate from the infusion device 202, such as, for example, the CCD 106 or the computing device 108.

Drive Cycle Occlusion Detection Techniques

Figure 3:
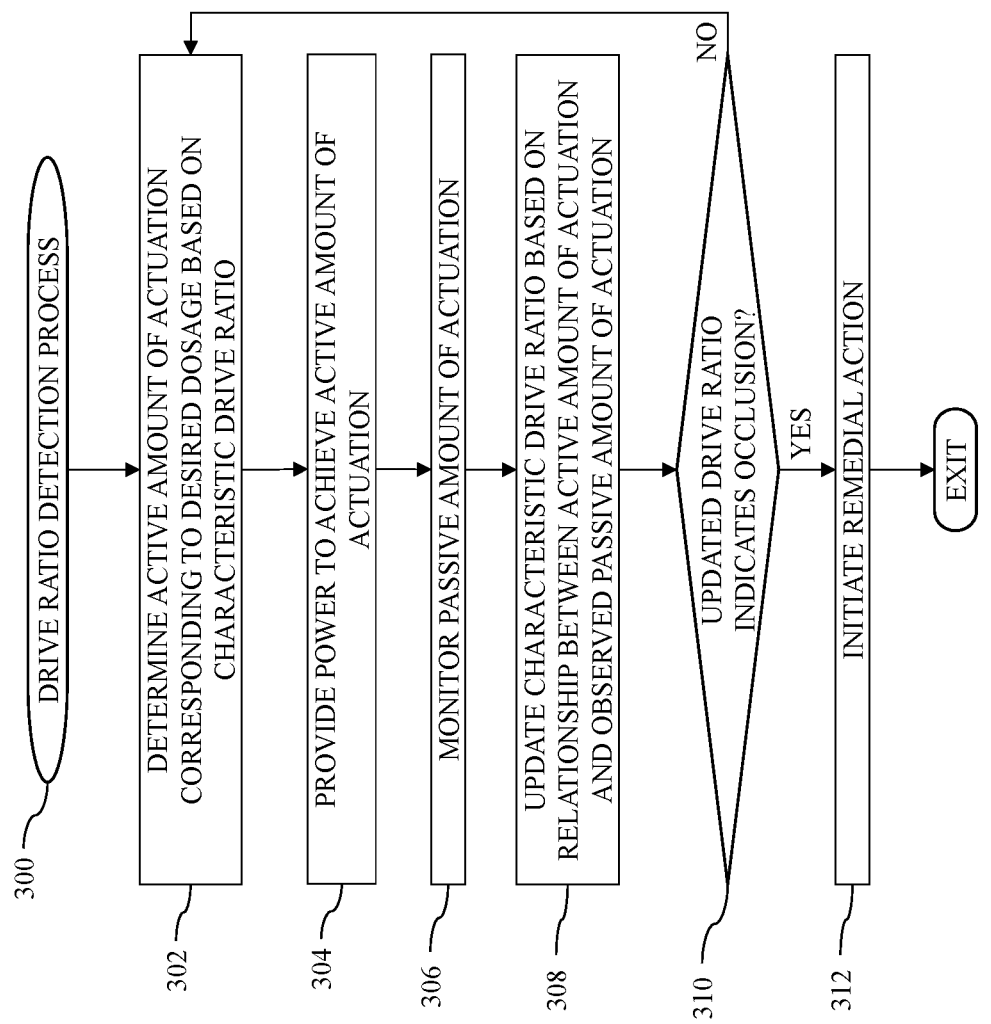
FIG. 3 is a flow diagram of an exemplary drive ratio occlusion detection process suitable for implementation in connection with operation of an infusion device in one or more exemplary embodiments.
Figures 4, 5:
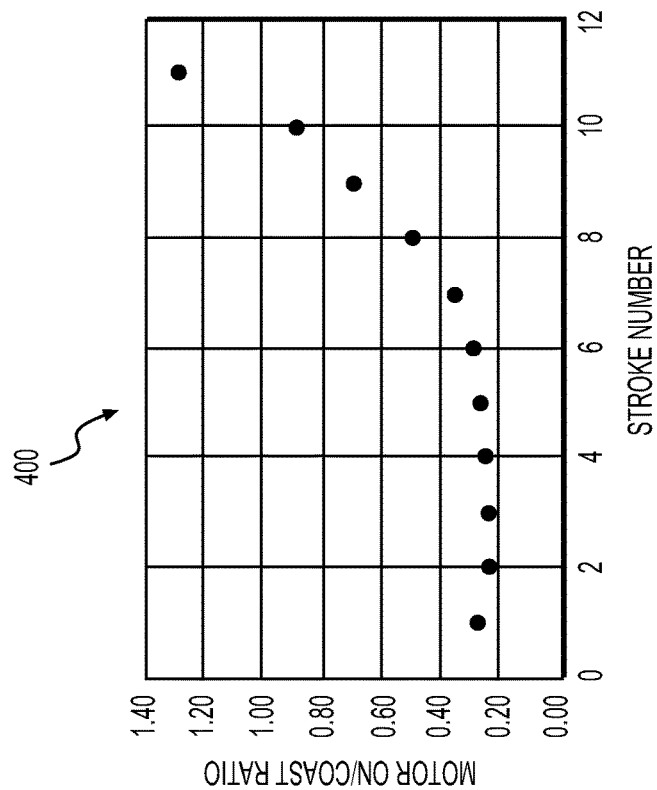
FIG. 4 is a graph depicting an exemplary relationship of the duty cycle of the actuation drive cycle with respect to actuation drive cycles in response to an occlusion condition in connection with an exemplary embodiment of the drive ratio occlusion detection process of FIG. 3.
FIG. 5 is a table corresponding to the graph depicted in FIG. 4 illustrating an exemplary embodiment of the drive ratio occlusion detection process of FIG. 3.

Referring now to FIGS. 3-5, in one or more exemplary embodiments, the actuator control module 212 and/or the pump control system 220 is capable of detecting an occlusion condition in a fluid path downstream of the plunger 217 based on the relationship between the active portion of a drive cycle for the actuator 232 and the passive portion of the drive cycle. In this regard, the active portion of the drive cycle corresponds to the relative duration or percentage of the drive cycle during which electrical power is applied to the actuator 232 (e.g., via the driver module 214) to produce rotation or other actuation of the actuator 232, while the passive portion of the drive cycle corresponds to the relative duration or percentage of the drive cycle during which actuator 232 continues rotating or otherwise actuating the plunger 217 after power flow to the actuator 232 is terminated. For example, the actuator control module 212 may be configured to operate the driver module 214 to provide current or power to the actuator 232 to initiate rotation or actuation and maintain operation of the actuator 232 for a particular amount of actuation before removing current or power and allowing the actuator 232 to effectively coast to a stop and achieve an additional amount of actuation. In this regard, a characteristic drive ratio for the actuator 232 is determined and utilized by the actuator control module 212 to calculate or otherwise determine a duration for the active portion of the drive cycle that results in a total amount of actuation corresponding to a commanded dosage.

As described in greater detail below, in response to an occlusion condition in the fluid path, the force opposing displacement of the plunger 217 produces a corresponding reactionary force that opposes further actuation of the actuator 232, which, in turn, decreases the passive amount of actuation that would otherwise result in the absence of such resistance. Accordingly, the relationship between the active amount of actuation and the passive amount of actuation during the drive cycle is monitored or otherwise analyze to detect a change in the relationship that is indicative of an occlusion condition in the fluid path.

FIG. 3 depicts an exemplary embodiment of a drive ratio detection process 300 suitable for implementation by a control system associated with an infusion device to detect an occlusion condition or other fluid path anomaly based on the relationship between active and passive portions of a drive cycle intended to deliver a commanded dosage of fluid. The various tasks performed in connection with the drive ratio detection process 300 may be performed by hardware, firmware, software executed by processing circuitry, or any combination thereof. For illustrative purposes, the following description refers to elements mentioned above in connection with FIGS. 1-2. For purposes of explanation, the drive ratio detection process 300 may be described herein primarily in the context of being implemented by the actuator control module 212 and/or the pump control system 220. It should be appreciated that the drive ratio detection process 300 may include any number of additional or alternative tasks, the tasks need not be performed in the illustrated order and/or the tasks may be performed concurrently, and/or the drive ratio detection process 300 may be incorporated into a more comprehensive procedure or process having additional functionality not described in detail herein. Moreover, one or more of the tasks shown and described in the context of FIG. 3 could be omitted from a practical embodiment of the drive ratio detection process 300 as long as the intended overall functionality remains intact.

The illustrated drive ratio detection process 300 begins by calculating or otherwise determining an amount of an upcoming drive cycle for actively applying electrical power to an actuator to achieve a desired dosage of fluid based on a characteristic drive ratio for the actuation system (task 302). In this regard, the characteristic drive ratio represents the relationship between the amount of actuation expected to be achieved after electrical power is no longer applied to the actuator relative to the amount of actuation achieved while electrical power is actively applied. For example, when the actuator 232 is realized as an electric motor, the inertia of a rotating rotor may result in the rotor continuing rotation and continuing to displace the plunger 217 after electrical power is no longer applied to the stator windings until the resistance applied by the plunger 217, friction, and/or other reactionary forces are sufficient to stop rotation of the rotor. In exemplary embodiments, the actuator control module 212 uses the characteristic drive ratio to calculate or otherwise determine the amount of active actuation based on a commanded dosage to account for the amount of passive actuation that is likely to result such that the sum of the active and passive actuation amounts corresponds to the commanded dosage. For example, if the characteristic drive ratio indicates that active actuation results in four times the amount of passive actuation (e.g., a ratio of 0.25), the active amount of actuation may be calculated as one-fifth of the total amount of actuation required to achieve a commanded dosage. Thus, if 100 encoder counts of actuation of a rotor are required to achieve a commanded dosage, the active amount of actuation may be determined as 20 encoder counts of actuation, with 80 encoded counts of passive actuation being expected based on the characteristic drive ratio (e.g., 20/80=0.25). In exemplary embodiments, the actuator control module 212 stores or otherwise maintains the characteristic drive ratio and dynamically updates or otherwise determines the characteristic drive ratio based on one or more preceding drive cycles, as described in greater detail below. Upon initialization or deployment of the infusion device 202, the actuator control module 212 may store a default or reference characteristic drive ratio that is subsequently overwritten and/or updated during operation of the infusion device 202.

After determining the active amount of actuation to be applied, the drive ratio detection process 300 continues by applying or otherwise providing electrical power to the actuator to achieve the determined amount of actuation (task 304). In this regard, the actuator control module 212 commands, signals, or otherwise operates the actuator driver module 214 to apply electrical energy from the energy source 218 to the actuator 232 to achieve the calculated amount of actuation. For example, if the actuator 232 is realized as a motor and the amount of actuation is determined as a number of encoder counts or other incremental rotations of a rotor of the motor, the actuator control module 212 may operate the actuator drive module 214 in a manner that causes the rotor to rotate and monitor the actuator sensing arrangement 216 (e.g., an encoder or other rotor position sensing arrangement) until the determined amount of actuation is achieved before commanding or otherwise operating the actuator drive module 214 to cease power flow to the motor 232. In exemplary embodiments, the actuator 232 is realized as a BLDC or BDC motor and the amount of actuation is determined as a duration of time, where the actuator control module 212 operates the actuator drive module 214 in a manner that causes the rotor of the motor to rotate for the calculated duration of time before commanding or otherwise operating the actuator drive module 214 to cease power flow to the motor 232.

The drive ratio detection process 300 continues by monitoring the passive amount of actuation resulting from the active amount of actuation (task 306). For example, when the actuator 232 is realized as a motor, after ceasing power flow to the stator windings of the motor 232, the actuator control module 212 may monitor a rotor position sensing arrangement 216, such as an encoder, to measure or otherwise observe the passive amount of rotation achieved by the rotor after power was removed from the stator windings. In other embodiments, the actuator control module 212 may monitor output of the sensing arrangement 216 to track or otherwise record the duration of time during which the rotor continues rotating after applying electrical power for a calculated duration of time.

Still referring to FIG. 3, the drive ratio detection process 300 calculates or otherwise determines an updated characteristic drive ratio for the actuator (or actuation system) based on the relationship between the active amount of actuation and the observed amount of passive actuation (task 308). For example, in one embodiment, the actuator control module 212 may update the characteristic drive ratio by dividing the active amount of actuation by the observed or measured amount of passive actuation. That said, there are numerous different ways to calculate, determine, or otherwise represent the relationship between the active and passive amounts of actuation, and the subject matter described herein is not limited to any particular implementation. The actuator control module 212 may store or otherwise maintain the updated characteristic drive ratio for subsequently determining future commands for operating the actuator driver module 214.

The drive ratio detection process 300 analyzes the updated characteristic drive ratio to identify, detect, or otherwise determine whether an occlusion condition exists based on the updated characteristic drive ratio, and in response to detecting an occlusion condition, initiating one or more remedial actions (tasks 310, 312). For example, in one embodiment, the updated characteristic drive ratio may be compared to a threshold value indicative of an occlusion condition in a fluid path. As described above, an occlusion in a fluid path results in a reactionary force that resists further displacement of the plunger 217, which, in turn, opposes further actuation of the actuator 232 via the mechanical coupling between the actuator 232 and the plunger 217, thereby decreasing the passive amount of actuation that would otherwise result in the absence of such resistance. For example, the reactionary force by increased fluid resistance may be transferred via the plunger 217 and any intervening gears or drive train components to transfer force to the rotor of the electric motor 232 that resists rotation of the rotor and thereby increases the rate at which the rotor stops coasting and comes to rest in the absence of power applied to the stator windings. Thus, the threshold value may then be calculated or otherwise determined as a drive ratio value that indicates a decrease in the passive amount of actuation relative to the active amount of actuation that is sufficiently likely to be attributable to an occlusion condition rather than variations in friction or other transient conditions.

In other embodiments, the drive ratio detection process 300 may analyze change or rate of change in the characteristic drive ratio across successive drive cycles to detect or otherwise identify when the characteristic drive ratio changes at a rate that is unlikely to be attributable to variations in friction or other transient conditions. In some embodiments, an occlusion condition may be detected when the change in the characteristic drive ratio across successive drive cycles is greater than a threshold value. In yet other embodiments, a matched filter may be utilized to detect an occlusion condition based on changes in the characteristic drive ratio across successive drive cycles. In this regard, the impulse response of the matched filter corresponds to or otherwise matches the expected (or anticipated) decrease in the amount of passive actuation when an occlusion condition exists or is otherwise exhibited. For example, in a similar manner as described in U.S. Pat. No. 9,402,949, the expected decrease in passive actuation in response to a fluid path occlusion provides a known signal response or template used to generate finite impulse response (FIR) filter coefficient values for the matched filter such that the impulse response of the matched filter reflects a reversed version of the expected characteristic drive ratio changes with respect to drive cycle. The actuator control module 212 may apply the matched filter to a sequence of characteristic drive ratios determined from preceding drive cycles to calculate or otherwise determine a filtered output as a function of the sequence of characteristic drive ratio values using the matched filter coefficients. The actuator control module 212 may then detect or otherwise identify an occlusion condition when the filtered output is greater than an occlusion threshold value.

When the actuator control module 212 detects an occlusion condition, the actuator control module 212 provides a notification of the fluid path occlusion to the pump control system 220 or another supervisory system or module (e.g., the CCD 106 and/or the computer 108). For example, the actuator control module 212 may generate an interrupt signal that is handled by the pump control system 220, which, in turn generates or otherwise provides one or more user notifications or alerts of the occlusion condition via the user interface 240 or another device (e.g., the CCD 106 and/or computing device 108). In practice, the pump control system 220 and/or the actuator control module 212 may perform other occlusion detection techniques, where the occlusion notification generated based on the drive ratio is utilized verify, confirm, or otherwise augment the other occlusion detection algorithms and/or techniques performed by the pump control system 220 and/or the actuator control module 212.

In the absence of detecting an occlusion condition, the loop defined by tasks 302, 304, 306, 308 and 310 repeats to deliver fluid in accordance with the updated characteristic drive ratio. In this regard, as the characteristic drive ratio fluctuates up or down due to variations in friction or other transient conditions that influence the amount of passive actuation, the active amount of actuation for subsequent drive cycles may be adjusted accordingly to compensate for previous over- and/or under-delivery of fluid. In one or more embodiments, in response to detecting an occlusion condition, the remedial action initiated by the detection process 300 is the performance of another occlusion detection process to validate, verify, or otherwise confirm the existence of the occlusion condition, thereby minimizing the likelihood of false positives, as described in greater detail below.

FIG. 4 depicts an exemplary graph of characteristic drive ratio values with respect to successive drive cycles and FIG. 5 is a corresponding table of drive cycle information for a scenario where an occlusion condition occurs or is otherwise introduced into the fluid path before or during the sixth drive cycle. In this regard, FIGS. 4-5 depict a situation where an infusion device (e.g., infusion device 102, 202) that incrementally delivers insulin dosages in 0.5 μL increments using a motor (e.g., actuator 232) where rotation of the rotor of the motor through 100 encoder counts corresponds to delivery of 0.5 μL of insulin.

For the first drive cycle, based on the initial characteristic drive ratio for the motor, the motor control module (e.g., actuator control module 212) calculates or otherwise determines an active amount of actuation of 22 encoder counts is expected to result in a total actuation of 100 encoder counts (e.g., task 302). Thereafter, the motor control module applies electrical power to the motor to actuate the rotor through 22 encoder counts (e.g., task 304) and then monitoring the encoder output to identify a passive amount of actuation of 80 encoder counts (e.g., task 306) before the motor coasts to a stop, resulting in a total number of encoder counts of 102. The updated characteristic drive ratio is determined by dividing the active amount of encoder counts by the number of observed passive encoder counts (e.g., 22/80=0.28) (e.g., task 308). When the drive ratio is less than an occlusion threshold value, the motor control module calculates or otherwise determines an active amount of actuation of 19 encoder counts for the next cycle based on the updated characteristic drive ratio. The active amount of actuation may also be determined in a manner that accounts for any over- or under-delivery of fluid during the preceding drive cycle. The motor control module continues operating the motor by applying input electrical power to the stator windings to achieve the active amount of actuation and then monitoring the resulting passive amount of actuation once electrical power is no longer applied to identify or otherwise detect presence of an occlusion condition.

In the illustrated scenario of FIGS. 4-5, an occlusion condition occurs before or during the sixth drive cycle, which results in the passive amount of actuation decreasing and the ratio of the active amount of actuation to the passive amount of actuation correspondingly increasing over successive cycles. For example, the passive amount of actuation may progressively decrease as the fluid path progressively becomes more obstructed and/or the reactionary force on the plunger progressively increases. As illustrated, the reduction in the amount of passive encoder counts per drive cycle results in a corresponding increase the characteristic drive ratio (e.g., the ratio of the active encoder counts to passive encoder counts). The increase in the drive ratio (or the decrease in the ratio of passive actuation to active actuation) combined with the amount of under-delivery results in the active amount of actuation increasing for the next drive cycle, which, in turn, results in an increased amount of reactionary fluid resistance forces on the plunger 217, which then further decreases the amount of passive actuation, such that the characteristic drive ratio increases relatively quickly after the occlusion condition as illustrated in FIGS. 4-5.

As described above, in some embodiments, the occlusion condition may be detected when the characteristic drive ratio exceeds a threshold value. For example, the occlusion detection threshold value may be set to a value of 0.4, which results in the occlusion condition being detected after the eight drive cycle results in an updated characteristic drive ratio of 0.5. It should be noted that there are numerous different ways in which the occlusion detection threshold value may be determined, and the subject matter described herein is not limited to any particular technique. By way of example, the occlusion detection threshold value may be statistically determined based on previous or historical characteristic drive ratio values (e.g., relative to a mean or median characteristic drive ratio value using one or more statistical metrics characterizing the distribution of the characteristic drive ratio values) to arrive at an occlusion detection threshold value that is unlikely to be attributable to normal variations or result in false positives.

In another embodiment, the relationship between characteristic drive ratio and drive cycle depicted in FIGS. 4-5 may be utilized as the known response or template utilized to generate a matched filter coefficient values such that the impulse response of a matched filter reflects a reversed version of the expected occlusion-induced increase to the characteristic drive ratio with respect to drive cycle. The matched filter may then be applied to the sequence of characteristic drive ratios to quickly detect (e.g., after the seventh drive cycle) and respond to the occlusion condition once the filtered output exceeds a detection threshold. It should be noted that the subject matter is not limited to matched filters, and in practice, more than one filter may be utilized, with different filters having different filter coefficients or characteristics for detecting different anomalous conditions. In some embodiments, different filter configurations may be utilized depending on the status or state of the infusion device 202 or the control system 200.

Although FIGS. 4-5 depict the active and passive amounts of actuation in terms of a number of incremental rotations of a rotor (e.g., encoder counts), the subject matter may be implemented in an equivalent manner for active and passive amounts of actuation in other domains. For example, for the first drive cycle, the active amount of actuation may be determined as a duration of time for applying input power to the actuator (e.g., 22 milliseconds) that is expected to result in a total duration of actuation (e.g., 100 milliseconds) that achieves a desired delivery of insulin. Thereafter, the motor control module applies electrical power to the actuator to operate the actuator for the determined duration of time before removing the input power and monitoring the remaining duration of passive actuation that occurs before the actuator stops, with the updated characteristic drive ratio being determined by dividing the active duration of actuation by the passive duration of actuation and then being analyzed using an occlusion detection threshold, a matched filter, or the like to detect an occlusion condition.

Actuation State-Based Detection Techniques

Referring now to FIGS. 6-9, in one or more exemplary embodiments, the actuator control module 212 and/or the pump control system 220 is capable of detecting an occlusion condition in a fluid path downstream of the plunger 217 based on one or more measurements obtained from the actuator sensing arrangement 216. In this regard, the force caused by an occlusion condition resisting displacement of the plunger 217 is capable of influencing the actuation state (or position) of the actuator 232 relative to an expected or commanded actuation state (or position). Accordingly, an occlusion condition may be detected based on the relationship between a commanded actuation state and a measured actuation state obtained via the actuator sensing arrangement 216.

For example, in one or more exemplary embodiments, the actuator 232 may be realized as a BLDC motor or another direct current (DC) motor that is commanded to produce a particular amount of actuation during a drive cycle and maintain the resulting actuation state between drive cycles. When an occlusion condition exists in a fluid path downstream of the plunger 217, the increased reactionary force applied to the plunger 217 by the downstream fluid relative to anon-occluded state is transferred to the rotor and results in a different final actuation state of the rotor compared to if there were not an occlusion. Accordingly, the actuator sensing arrangement 216 may be realized as a position sensing arrangement capable of measuring the position or actuation state of the BLDC motor rotor to allow an occlusion condition to be detected when the difference between the measured position (or state) and the previously-commanded position (or state) is greater than an occlusion detection threshold.

Figure 6:
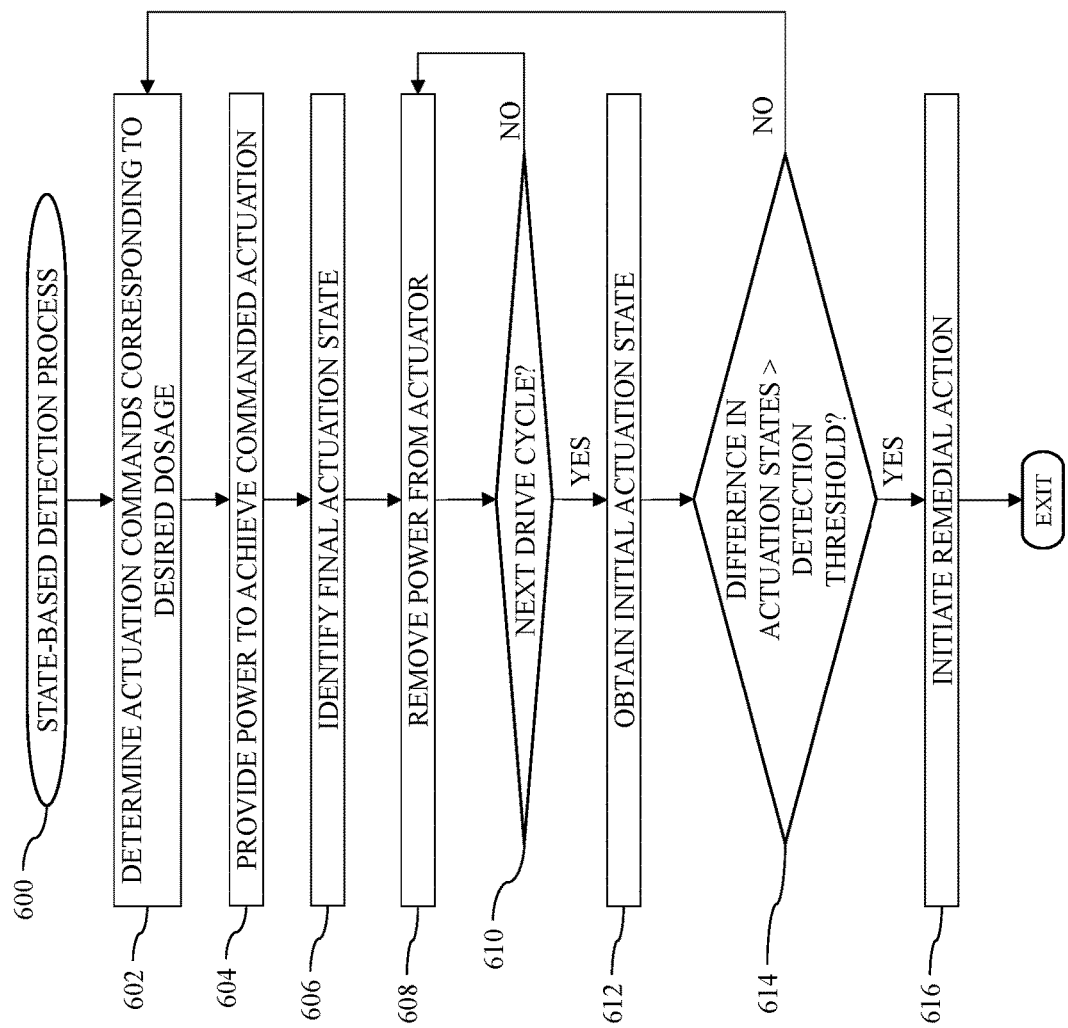
FIG. 6 is a flow diagram of an exemplary state-based detection process suitable for implementation in connection with operation of an infusion device in one or more exemplary embodiments.
Figure 8:
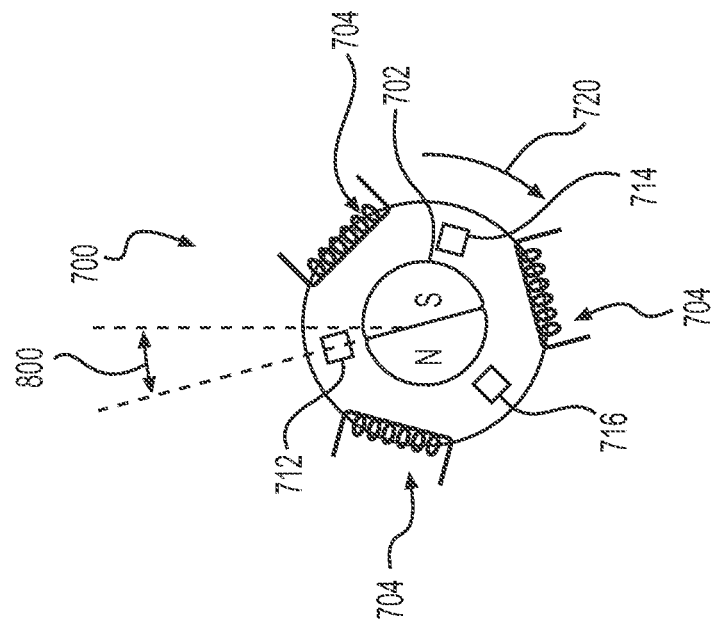
FIGS. 7-8 depict top plan views of a three-phase motor illustrating the state-based detection process of FIG. 6 in an exemplary embodiment.
Figure 7:
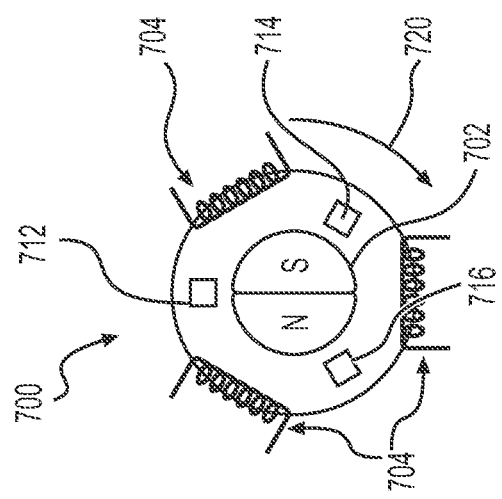

For purposes of explanation, FIGS. 6-8 may be described herein in the context of the actuator 232 being realized as a BLDC motor; however, it should be noted that the subject matter is not limited to BLDC motors and may be implemented in an equivalent manner for other types of motors or actuators. Additionally, the subject matter may be described herein in the context of the actuator sensing arrangement 216 being realized as a Hall effect position sensing arrangement including one or more Hall effect sensors; however, it should be noted that the subject matter is not limited to Hall effect sensors and may be implemented in an equivalent manner using rotary encoders, resolvers, or other types of position sensors.

FIG. 6 depicts an exemplary embodiment of a state-based detection process 600 suitable for implementation by a control system associated with an infusion device to detect an occlusion condition or other fluid path anomaly based on the relationship between a measured actuation state and a commanded actuation state for an actuator. The various tasks performed in connection with the state-based detection process 600 may be performed by hardware, firmware, software executed by processing circuitry, or any combination thereof. For illustrative purposes, the following description refers to elements mentioned above in connection with FIGS. 1-2. For purposes of explanation, the state-based detection process 600 may be described herein primarily in the context of being implemented by the actuator control module 212 and/or the pump control system 220. It should be appreciated that the state-based detection process 600 may include any number of additional or alternative tasks, the tasks need not be performed in the illustrated order and/or the tasks may be performed concurrently, and/or the state-based detection process 600 may be incorporated into a more comprehensive procedure or process having additional functionality not described in detail herein. Moreover, one or more of the tasks shown and described in the context of FIG. 6 could be omitted from a practical embodiment of the state-based detection process 600 as long as the intended overall functionality remains intact.

Referring to FIG. 6, with continued reference to FIG. 2, the state-based detection process 600 initializes or otherwise begins by calculating or otherwise determining an amount of actuation to be provided corresponding to a desired dosage command (task 602). For example, in the context of a BLDC motor 232, the pump control system 220 may provide an amount of fluid to be delivered to the motor control module 212, which, in turn, converts the commanded dosage into a corresponding degree of commanded motor rotations to achieve displacement of the plunger 217 corresponding to that commanded amount of fluid. Thereafter, the state-based detection process 600 continues by providing input electrical power to the actuator to change the actuation state and achieve the commanded amount of actuation (task 604). For example, the motor control module 212 may signal, command, instruct, or otherwise operate the motor driver module 214 to sequentially apply voltage and/or current from the energy source 218 to the various sets of stator windings of the BLDC motor 232 in the appropriate order to cause rotor of the BLDC motor 232 rotate by the commanded number of motor rotations from the initial position or state of the rotor.

After operating the actuator, the state-based detection process 600 measures, obtains, or otherwise identifies the final actuation state at the end of the drive cycle before removing input electrical power from the actuator (tasks 606, 608). For example, after operating the driver module 214 to sequentially apply power to subsets of the stator windings of the BLDC motor 232 to advance the rotor through the number of degrees corresponding to the commanded dosage, the motor control module 212 may obtain the measured position or state of the rotor from the rotor sensing arrangement 216 while maintaining the final configuration of the motor driver module 214 to maintain the rotor in a substantially stationary position while obtaining the measured position. In other embodiments, the motor control module 212 may simply identify the final actuation state as the final commutation state provided by the motor driver module 214 at the end of the drive cycle. After obtaining the final (or commanded) actuation state corresponding to the end of the drive cycle, the motor control module 212 commands, signals, or otherwise instructs the motor driver module 214 to cease providing electrical power to the stator windings of the motor 232, for example, by opening switching elements of the motor driver module 214 to isolate the stator windings from the energy source 218. Thereafter, the motor control module 212 and/or motor driver module 214 may maintain the stator windings in a de-energized state until the next drive cycle.

When the state-based detection process 600 identifies the start of a next drive cycle, the state-based detection process 600 measures, obtains, or otherwise identifies the initial actuation state at the start of the drive cycle and verifies or otherwise confirms the difference between the initial actuation state and the final actuation state from the preceding drive cycle is less than an occlusion detection threshold prior to operating the actuator (tasks 610, 612, 614). For example, in response to receiving a dosage command from the pump control system 220, the motor control module 212 may obtain a current measurement of the position or state of the rotor from the rotor sensing arrangement 216 prior to operating the motor driver module 214 to implement the dosage command. In this regard, in response to an occlusion condition, the reactionary force applied to the plunger 217 opposing displacement in the actuation direction may be transferred back to the rotor of the BLDC motor 232 (e.g., via gears or other drive train components) and cause displacement of the rotor in the reverse direction opposite the actuation direction once input power is no longer applied to the stator windings of the motor 232. Thus, when the difference between the measured rotor position at the start of a drive cycle and the measured rotor position at the end of the preceding drive cycle is greater than a threshold amount, the motor control module 212 detects or otherwise identifies an occlusion condition. In a similar manner as described above, the occlusion threshold value may be chosen based on the resolution of the sensing arrangement 216 and/or other factors to account for potential transient variations to minimize the probability or likelihood of false positives.

As described above, in response to detecting an occlusion condition, the state-based detection process 600 may initiate or otherwise perform one or more remedial actions (task 616). For example, the actuator control module 212 may generate an interrupt signal that is handled by the pump control system 220, which, in turn generates or otherwise provides one or more user notifications or alerts of the occlusion condition via the user interface 240 or another device. In the absence of detecting an occlusion condition, the loop defined by tasks 602, 604, 606, 608, 610, 612 and 614 repeats to continually monitor the actuation state or position of the actuator 232 before and after each drive cycle to detect an occlusion condition based on changes in the actuation state or position between drive cycles.

FIGS. 7-8 depict a top plan view of a BLDC motor 700 and rotor sensing arrangement 710 suitable for use with the state-based detection process 600 of FIG. 6. The BLDC motor 700 includes a permanent magnet rotor 702 and three sets of stator windings 704 to which a voltage or current may be applied in a sequence of commutation states based on the orientation of the permanent magnet rotor 702 to rotate the rotor 702 by a desired amount of actuation (e.g., a desired rotation) in a fluid delivery direction 720. Although not illustrated, the rotor 702 may engage gears or other drive train components that translate the rotational displacement of the rotor 702 into linear displacement of a plunger (e.g., plunger 217), as will be appreciated in the art. In the illustrated embodiment, the sensing arrangement 710 includes three Hall effect sensors 712, 714, 716 positioned between adjacent pairs of stator windings 704 to detect or otherwise indicate the orientation of the rotor 702. For example, FIG. 7 may depict the final actuation state (or commutation state) of the rotor 702 where the rotor 702 is aligned such that Hall effect sensors 712, 716 produce an output signal indicative of a magnetic north pole of the permanent magnet rotor 702 and the Hall effect sensor 714 produces an output signal indicative of the magnetic south pole of the rotor 702.

Referring to FIG. 8, with continued reference to FIGS. 6-7, after removing input power to the stator windings 704, an occlusion condition may exert a force on the plunger 217 that resists displacement in the actuation direction, which, in turn, is transferred back to the rotor 702 to rotate the rotor 702 in the reverse direction when the input power is removed and the stator windings 704 are de-energized. Thereafter, at the start of the next drive cycle, the motor control module 212 may obtain a measured position or state of the rotor 702 from the sensing arrangement 710, where only the Hall effect sensor 716 produces an output signal indicative of the magnetic north pole and the other two Hall effect sensors 712, 714 produce an output signal indicative of the magnetic south pole of the rotor 702 (e.g., task 612). When the difference (e.g., angular displacement 800) between the previously obtained final actuation state at the end of the preceding drive cycle depicted in FIG. 7 and the current actuation state upon initiation of the next drive cycle depicted in FIG. 8 is greater than an occlusion detection threshold, the motor control module 212 may detect an occlusion condition and initiate one or more remedial actions as described above.

Figure 9:
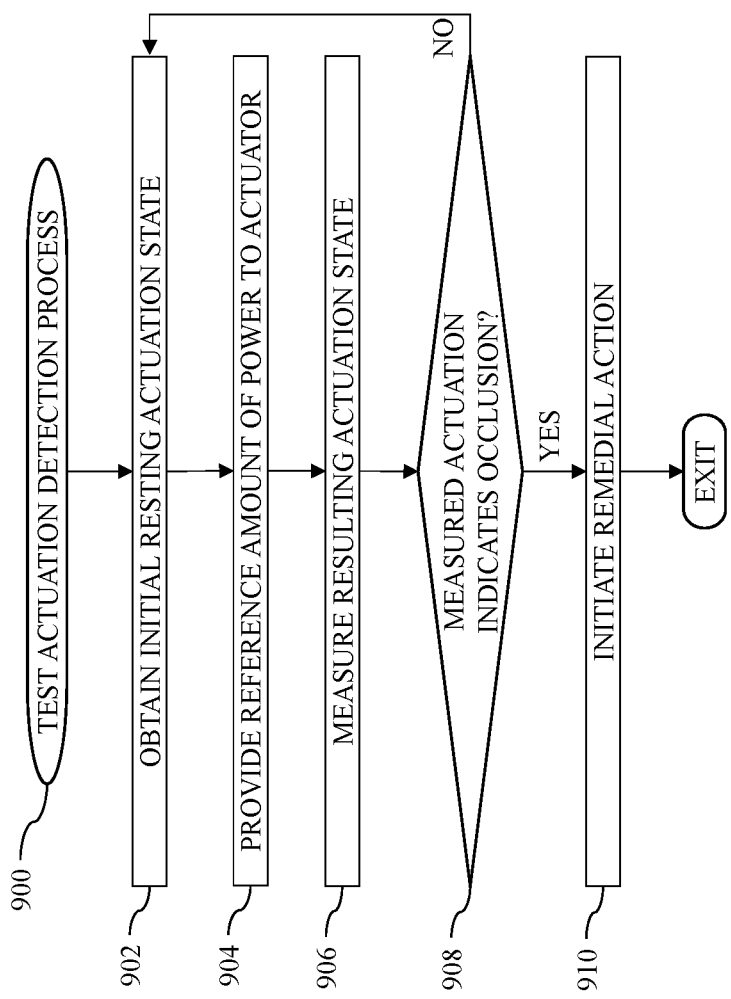
FIG. 9 is a flow diagram of an exemplary test actuation detection process suitable for implementation in connection with operation of an infusion device in one or more exemplary embodiments.

In other embodiments, the actuator 232 may be energized and de-energized independent of a drive cycle to test or probe for a potential occlusion condition. In this regard, FIG. 9 depicts an exemplary embodiment of a test actuation detection process 900 suitable for implementation by a control system associated with an infusion device to detect an occlusion condition or other fluid path anomaly based on the relationship between a measured actuation state and a reference actuation state for an actuator. The various tasks performed in connection with the test actuation detection process 900 may be performed by hardware, firmware, software executed by processing circuitry, or any combination thereof. For illustrative purposes, the following description refers to elements mentioned above in connection with FIGS. 1-2 and 7-8. For purposes of explanation, the test actuation detection process 900 may be described herein primarily in the context of being implemented by the actuator control module 212 and/or the pump control system 220. It should be appreciated that the test actuation detection process 900 may include any number of additional or alternative tasks, the tasks need not be performed in the illustrated order and/or the tasks may be performed concurrently, and/or the test actuation detection process 900 may be incorporated into a more comprehensive procedure or process having additional functionality not described in detail herein. Moreover, one or more of the tasks shown and described in the context of FIG. 9 could be omitted from a practical embodiment of the test actuation detection process 900 as long as the intended overall functionality remains intact.

The test actuation detection process 900 begins by measuring, obtaining, or otherwise identifying an initial resting actuation state of the actuator prior to applying or otherwise providing a reference amount of input power to the actuator to actuate the actuator from the initial actuation state (tasks 902, 904). In this regard, the reference amount of input power is chosen to be an amount of voltage and/or current to be applied that is unlikely to result in delivery of fluid but sufficient to achieve a measurable amount of displacement or rotation of a rotor or other actuatable component in the absence of an occlusion condition, for example, due to slack, compliance or other tolerances within the drive train or other linkages between the actuator 232 and the plunger 217 (e.g., deflection or other bending of gears, reservoir expansion, and/or the like). For example, referring to FIGS. 7-8, the reference amount of input power may be chosen to be an amount that is sufficient to result in at least one Hall effect sensor 712, 714, 716 changing its state in the absence of an occlusion condition but less than the amount of power that would result in two of the Hall effect sensors 712, 714, 716 changing states. That said, in other embodiments, the reference amount of input power may be chosen to be the amount of input power required to overcome static friction and/or other forces to initiate rotation of the rotor or otherwise start the motor 232. Based on the initial commutation state of the motor 232, 700, the reference voltage and/or current is applied to the appropriate subset of stator windings 704 that would otherwise advance the position of the rotor 702 in the fluid delivery direction.

While the reference amount of power is applied, the test actuation detection process 900 measures, obtains, or otherwise identifies the resulting actuation state for the actuator (task 906). In this regard, the motor control module 212 may obtain the measured position of the rotor 702 of the motor 232, 700 via the rotor sensing arrangement 216, 710 while the reference input power is applied to the motor 232, 700 before operating the motor driver module 214 to remove the input power and de-energize the stator windings 704.

Thereafter, the test actuation detection process 900 detects or otherwise identifies whether an occlusion condition exists based on the measured amount of actuation resulting from the applied reference power (task 908). In this regard, when an occlusion condition exists, the reactionary force on the plunger 217 may eliminate the slack in the drive train that may otherwise be present when the motor 232 is in a de-energized state, such that the amount of rotation or actuation in response to the reference input power is reduced relative to what it would otherwise be in the absence of an occlusion condition. In one embodiment, an occlusion condition is detected when the difference between the measured actuation state while the reference input power was applied to the motor 232 and the initial resting actuation state is less than a threshold amount of actuation that should otherwise occur in the absence of an occlusion condition. For example, if the reference input power fails to result in any of the Hall effect sensors 712, 714, 716 changing their states, the motor control module 212 may determine that an occlusion condition exists. In response to detecting an occlusion condition, the test actuation detection process 900 may initiate or otherwise perform one or more remedial actions in a similar manner as described above (task 910). Depending on the embodiment, the test actuation detection process 900 could be performed in between drive cycles, prior to each drive cycle, on a periodic basis (e.g., hourly), or in response to some other stimulus, and the subject matter described herein is not limited to any particular means or manner for scheduling or triggering the test actuation detection process 900.

Motor Dynamics Detection Techniques

Figure 10:
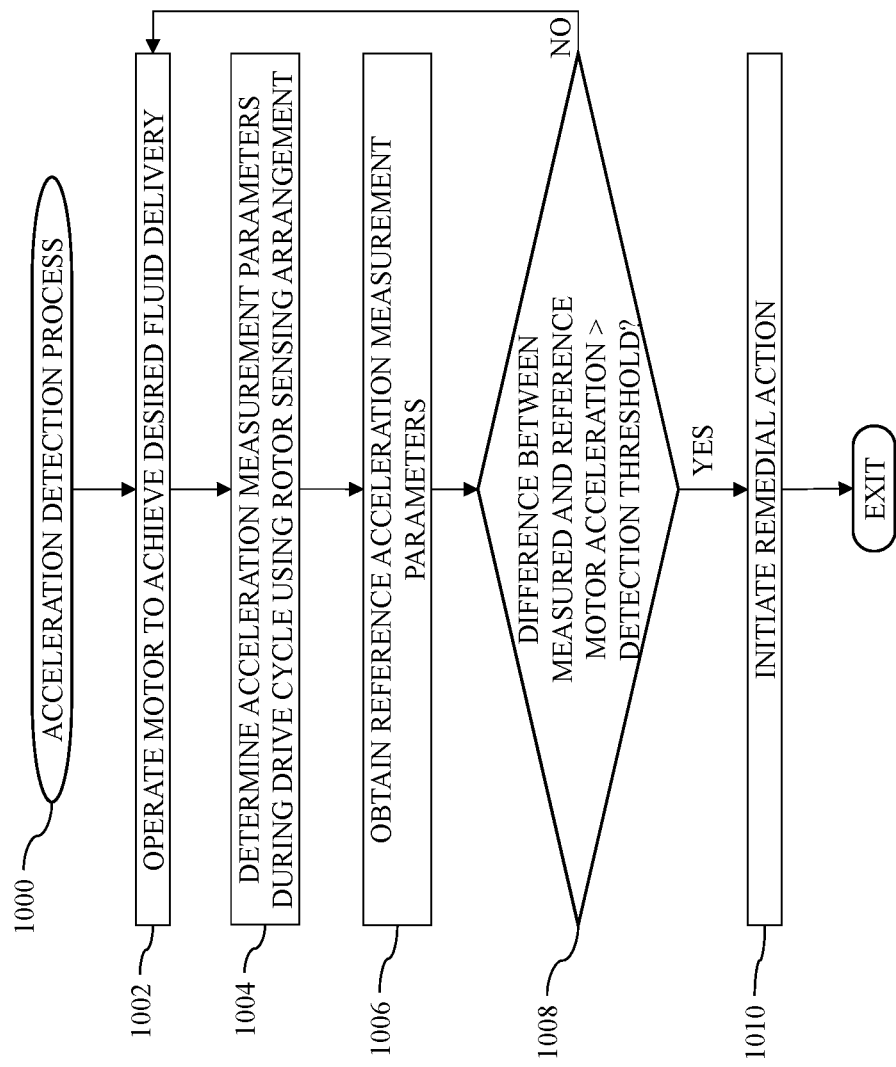
FIG. 10 is a flow diagram of an exemplary acceleration detection process suitable for implementation in connection with operation of an infusion device in one or more exemplary embodiments.
Figure 11:
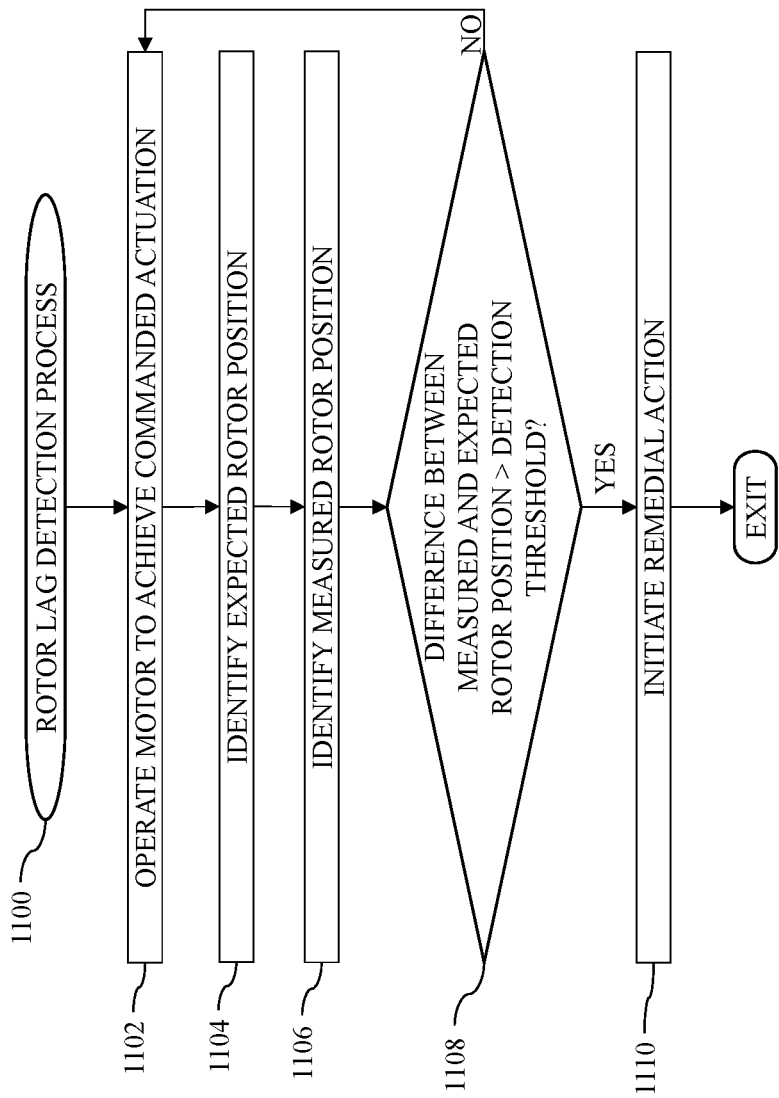
FIG. 11 is a flow diagram of an exemplary rotor lag detection process suitable for implementation in connection with operation of an infusion device in one or more exemplary embodiments.

Referring now to FIGS. 10-11, in one or more exemplary embodiments, the actuator control module 212 and/or the pump control system 220 is capable of detecting an occlusion condition in a fluid path downstream of the plunger 217 based on changes in the dynamics of the actuator 232. For example, when the actuator 232 is realized as a motor, the force caused by an occlusion condition resisting displacement of the plunger 217 is capable of influencing the acceleration or rotational velocity of the rotor. Accordingly, an occlusion condition may be detected based on changes to the rotor dynamics by monitoring the measured rotor position output by the rotor sensing arrangement 216. For purposes of explanation, the subject matter of FIGS. 10-11 is described in the context of the actuator 232 being realized as a motor and the actuator sensing arrangement 216 being realized as a rotor sensing arrangement, however, it should be appreciated that the subject matter is not necessarily so limited and could be implemented in an equivalent manner for other actuators and/or sensors.

FIG. 10 depicts an exemplary embodiment of an acceleration detection process 1000 suitable for implementation by a control system associated with an infusion device to detect an occlusion condition or other fluid path anomaly based on acceleration changes. The various tasks performed in connection with the acceleration detection process 1000 may be performed by hardware, firmware, software executed by processing circuitry, or any combination thereof. For illustrative purposes, the following description refers to elements mentioned above in connection with FIGS. 1-2. For purposes of explanation, the acceleration detection process 1000 may be described herein primarily in the context of being implemented by the actuator control module 212 and/or the pump control system 220. It should be appreciated that the acceleration detection process 1000 may include any number of additional or alternative tasks, the tasks need not be performed in the illustrated order and/or the tasks may be performed concurrently, and/or the acceleration detection process 1000 may be incorporated into a more comprehensive procedure or process having additional functionality not described in detail herein. Moreover, one or more of the tasks shown and described in the context of FIG. 10 could be omitted from a practical embodiment of the acceleration detection process 1000 as long as the intended overall functionality remains intact.

The illustrated acceleration detection process 1000 initializes or otherwise begins by operating the actuator to achieve a desired delivery of fluid and calculating or otherwise determining acceleration parameters for the drive cycle based on the output of the actuator sensing arrangement (tasks 1002, 1004). For example, while the motor control module 212 operates the motor driver module 214 to actuate the rotor of the motor 232 by an amount configured to deliver a desired dosage of fluid, the output of the rotor sensing arrangement 216 may be continually monitored or sampled to obtain a sequence of measured rotor positions, which, in turn may be utilized to calculate or otherwise determine one or more acceleration parameters for the rotor during the drive cycle. Based on the changes in the measured rotor position across successive samples, a corresponding measured acceleration value can be determined, which, in turn may be stored in association with the respective sample. In this regard, the motor control module 212 may obtain a sequence of measured acceleration values that characterize the dynamics of the rotor during the preceding drive cycle. In various embodiments, the sequence of measured acceleration values may also be analyzed to identify or otherwise determine the maximum forward acceleration value during the drive cycle, the maximum reverse acceleration (or deceleration) value during the cycle, and/or the like.

The acceleration detection process 1000 identifies or otherwise obtains one or more reference acceleration parameters for the rotor and then detects or otherwise identifies the presence of an occlusion condition based on a relationship between reference acceleration parameter(s) and the measured acceleration parameter(s) for the preceding drive cycle (tasks 1006, 1008). When the observed or measured acceleration is indicative of an occlusion condition, the acceleration detection process 1000 initiates one or more remedial actions as described above (task 1010).

In one or more embodiments, the dynamics of the motor 232 during a non-occluded state may be characterized for a particular combination of energy source voltage level, driver module switching frequency, rotor position sampling frequency, and/or the like by operating the motor 232 with a non-occluded fluid path to identify nominal or characteristic values for the maximum forward acceleration value, the maximum deceleration value, and/or the like. In some embodiments, where the motor 232 is operated to deliver fluid via a series of fixed drive cycles (e.g., 0.5 µL dosages) the motor 232 may be characterized to obtain a reference sequence of acceleration values for a complete drive cycle for delivering that fixed dosage without an occlusion condition.

To detect an occlusion condition, the motor control module 212 compares the measured acceleration parameters for the preceding drive cycle to the reference acceleration parameters and detects an occlusion condition based on the difference. For example, if the maximum forward acceleration during the preceding drive cycle is less than the reference maximum forward acceleration during a non-occluded drive cycle by more than a detection threshold amount, the motor control module 212 may detect an occlusion condition. In this regard, the detection threshold may be chosen to be an amount that is unlikely to be attributable to variations in friction or other transient conditions. Additionally, or alternatively, if the maximum deceleration during the preceding drive cycle is greater than the average or nominal maximum deceleration during a non-occluded drive cycle by more than a deceleration detection threshold amount, the motor control module 212 may detect an occlusion condition. In this regard, the reactionary force generated by an occlusion condition may cause the rotor to decelerate faster than normal for a non-occluded state.

As another example, an occlusion condition could be detected based on the difference between the sequence of measured acceleration values for the preceding drive cycle and the reference sequence of acceleration values. In this regard, the reference sequence of acceleration values may function as a template signal for the characteristic acceleration dynamics of the rotor in a non-occluded state, where sufficient deviations in the measured acceleration signal relative to the reference acceleration signal are indicative of an occlusion condition. For example, in response to an occlusion condition providing a force resisting displacement of the plunger 217, the forward acceleration values throughout the drive cycle are likely to be reduced relative to a non-occluded state, while the deceleration values throughout the drive cycle are likely to be increased relative to a non-occluded state. Thus, the amount or degree to which the sequence of measured acceleration values for the preceding drive cycle is shifted down relative to the reference sequence of acceleration values may be monitored by the motor control module 212 and utilized to detect an occlusion condition. It should be noted that any number of different acceleration-based occlusion detection references or criteria may be utilized in combination with one another, for example, to minimize or eliminate false positives by requiring both the measured forward acceleration and the measured deceleration to confirm or otherwise indicate an occlusion condition.

In one or more embodiments, the acceleration detection process 1000 may be performed to validate, verify, or otherwise confirm presence of an occlusion condition detected using the drive ratio detection process 300, the state-based detection process 600, and/or the test actuation process 900. In this regard, the acceleration detection process 1000 may be configured or otherwise performed in the context of a motor rewind or other actuation in the direction opposite the fluid delivery direction of actuation. For example, the test actuation process 900 may be performed between drive cycles to initially detect an occlusion condition. To confirm the occlusion condition, the acceleration detection process 1000 may be automatically initiated or otherwise performed in connection with a rewind of the motor 232 to validate the occlusion detection. In this regard, the motor control module 212 operates the motor driver module 214 to rotate the rotor of the motor 232 in the direction opposite the delivery direction to retract the plunger 217. During the rewind, the output of the rotor sensing arrangement 216 may be continually monitored or sampled to obtain a sequence of measured rotor positions, which, in turn may be utilized to calculate or otherwise determine one or more acceleration parameters for the rotor during the rewind operation. The observed or measured rewind acceleration parameters may then be compared to reference rewind acceleration parameters to validate the occlusion condition, for example, when the measured maximum rotor acceleration in the rewind direction is greater than a reference maximum rotor acceleration in the rewind direction, and/or the like.

When the acceleration detection process 1000 is used to validate or confirm an occlusion condition detected using another detection process 300, 600, 900, such other process 300, 600, 900 may forgo initiating a remedial action until it is confirmed via the acceleration detection process 1000. In this regard, when the acceleration detection process 1000 does not detect an occlusion condition during the rewind operation, the acceleration detection process 1000 may effectively suppress or otherwise override the remedial action that would have otherwise been initiated by another detection process 300, 600, 900. Moreover, in the absence of an occlusion condition, the motor control module 212 may be configured to rotate the rotor of the motor 232 in the fluid delivery direction to advance the plunger 217 back towards its initial state at the start of the acceleration detection process 1000 (e.g., the rotor position at the end of the preceding drive cycle).

FIG. 11 depicts an exemplary embodiment of a rotor lag detection process 1100 suitable for implementation by a control system associated with an infusion device to detect an occlusion condition or other fluid path anomaly based on rotor dynamics. The various tasks performed in connection with the rotor lag detection process 1100 may be performed by hardware, firmware, software executed by processing circuitry, or any combination thereof. For illustrative purposes, the following description refers to elements mentioned above in connection with FIGS. 1-2. For purposes of explanation, the rotor lag detection process 1100 may be described herein primarily in the context of being implemented by the actuator control module 212 and/or the pump control system 220. It should be appreciated that the rotor lag detection process 1100 may include any number of additional or alternative tasks, the tasks need not be performed in the illustrated order and/or the tasks may be performed concurrently, and/or the acceleration detection process 1000 may be incorporated into a more comprehensive procedure or process having additional functionality not described in detail herein. Moreover, one or more of the tasks shown and described in the context of FIG. 11 could be omitted from a practical embodiment of the rotor lag detection process 1100 as long as the intended overall functionality remains intact.

The illustrated rotor lag detection process 1100 initializes or otherwise begins by operating the motor to achieve a desired delivery of fluid, and while operating the motor, continually identifying or otherwise determining an expected rotor position, a measured rotor position, and whether the difference between the expected rotor position and the measured rotor position is greater than an occlusion detection threshold (tasks 1102, 1104, 1106, and 1108). In this regard, the rotor lag detection process 1100 may be implemented in connection with a stepper motor, brushless direct current (BLDC) motor, or other electrically commutated motor where the stator windings are sequentially energized and/or de-energized based on the position of the rotor. Thus, based on the angular position or orientation of the rotor provided by the rotor sensing arrangement 216, the motor control module 212 operates the motor driver module 214 to provide input power to an appropriate subset of the stator windings of the motor 232 to rotate the rotor in the actuation direction from the current angular position. When an occlusion condition exists, the reactionary force on the plunger 217 causes the rotor position to lag the expected position for the rotor based on the commutation state of the of the motor 232. Accordingly, when the difference between measured rotor position and the expected position of the rotor during operation of the motor is greater than an occlusion detection threshold, the rotor lag detection process 1100 detects an occlusion condition and initiates a remedial action in a similar manner as described above (task 1110).

For example, in one embodiment, the expected rotor position is determined based on the commutation state of the stator windings of the motor 232. In this regard, the actuator control module 212 may detect an occlusion condition when the difference between the angular position or orientation of the rotating magnetic field corresponding to the commutation state and the observed or measured angular position or orientation of the rotor obtained via the rotor position sensing arrangement 216 is greater than an occlusion detection threshold. In yet other embodiments, an expected angular position or orientation of the rotor may be determined relative to or based on the angular position or orientation of the rotating magnetic field corresponding to the commutation state, where the difference between the expected rotor position and the measured rotor position provided by the rotor sensing arrangement 216 indicates the amount by which the rotor lags the expected rotor position. In a similar manner, when the amount of lag between the expected rotor position and the measured or observed rotor position is greater than a threshold amount that is unlikely to be attributable to variations in friction or other transient conditions, the actuator control module 212 detects an occlusion condition and provides a corresponding indication to the pump control system 220, the user interface 240, and/or the like.

It should be noted that similar to the acceleration detection process 1000, the rotor lag detection process 1100 may be implemented in connection with one or more other occlusion detection processes 300, 600, 900. For example, the rotor lag detection process 1100 and the state-based detection process 600 and/or the test actuation detection process 900 may be implemented in concert with one another in the context of a stepper motor, brushless direct current (BLDC) motor, or other electrically commutated motor. In this regard, the rotor lag detection process 1100 may be performed to provide an initial indication of an occlusion condition during a drive cycle, while the state-based detection process 600 and/or the test actuation detection process 900 is performed prior to the next drive cycle to confirm validity of the occlusion condition detected by the rotor lag detection process 1100.

Occlusion Detection Based on Rotor Axis Tilting

Figure 12:
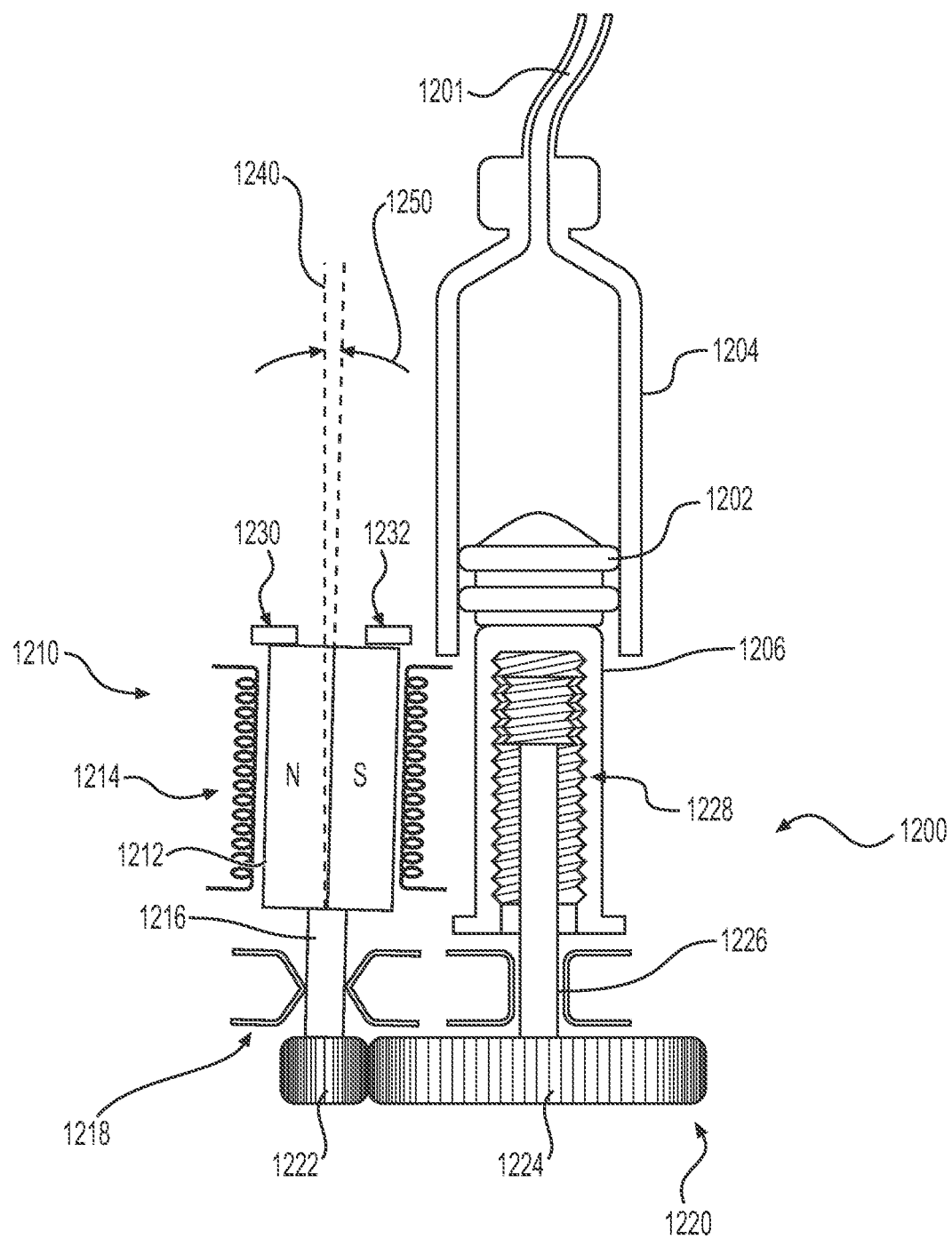
FIG. 12 is a cross-sectional view of a fluid delivery system suitable for use with an infusion device for detecting an anomalous condition based on an orientation of the rotational axis of a rotor in one or more exemplary embodiments.

Referring now to FIG. 12, in one or more exemplary embodiments, the actuator control module 212 and/or the pump control system 220 is capable of detecting an occlusion condition in a fluid path downstream of the plunger 217 based on changes in the physical orientation of the actuator 232. For example, when the actuator 232 is realized as a motor, the reactionary force caused by an occlusion condition resisting displacement of the plunger 217 increases the torque on the gears or other drive train components, which, in turn may generate a force capable of shifting or otherwise altering the physical orientation of the rotor. In this regard, an increase in torque between gears results in a force that repels the gears from one another due to the shape or form of the gear teeth. The resulting force may be transferred to a rotor engaged with one of the gears, which, in turn, influences the physical orientation of the rotor.

FIG. 12 depicts a cross-sectional view of an exemplary fluid delivery system 1200 suitable for use in an infusion device. The fluid delivery system 1200 includes a motor 1210 (e.g., actuator 232) that is coupled to a plunger 1202 (e.g., plunger 217) disposed within a fluid reservoir 1204 via a drive system 1220 that is configured to convert rotational motor motion to a translational displacement of a slide 1206 in an axial direction, and thereby engaging and displacing the plunger 1202 of the reservoir 1204 in the axial direction to dispense fluid from the reservoir 1204. The motor 1210 includes a rotor 1212 including one or more permanent magnets mounted to a rotary shaft 1216 defining a central axis of rotation (or rotational axis) that is aligned with the rotary shaft 1216 in an axial direction. The rotor 1212 is disposed within a stator including sets of windings 1214 that are circumferentially disposed about the rotor 1212 in a conventional manner. In the illustrated embodiment, rotary shaft 1216 extends from the housing of the motor 1210 to a distal end that engages a gear 1222 of the drive system 1220.

In the illustrated embodiment, the gear 1222 is realized as a spur gear that engages another spur gear 1224 that is mounted to an end of a rotatable shaft 1226 of a drive screw 1228. For purposes of explanation, the spur gear 1222 is alternatively referred to herein as the motor output gear. The drive screw 1228 includes threads that mate with threads internal to the slide 1206. Rotation of the drive screw 1228 in the fluid delivery actuation direction causes the slide 1206 to extend and advance the plunger 1202 in an axial direction to force fluid from the reservoir 1204 via a fluid path 1201. In this regard, applying electrical power to the stator windings 1214 to actuate the rotor 1212 in the fluid delivery direction results in rotation of the shaft 1216 and spur gear 1222, which, in turn rotates the spur gear 1224 and the shaft 1226 to advance the slide 1206 and plunger 1202.

In the illustrated embodiment, the rotor shaft 1216 is surrounded by a bushing 1218 disposed between the motor 1210 and the motor output gear 1222 that restricts lateral displacement of the rotor shaft 1216. At the same time, the motor output gear 1222 is capable of being displaced laterally away from the spur gear 1224, which, in turn results in the rotational axis of the tilting or otherwise deviating from a reference rotational axis 1240 by some amount of angular displacement 1250. In this regard, when an occlusion condition exists with respect to the fluid path 1201, the resulting reactionary force on the plunger 1202 increases the torque at the spur gear 1224 which results in a lateral force that displaces the motor output gear 1222 away from the spur gear 1224, thereby increasing the tilt or angular displacement 1250 of the rotational axis of the rotor 1212 and/or rotor shaft 1216 relative to the reference rotor axis 1240 corresponding to a non-occluded state. Accordingly, an occlusion condition may be detected when the amount of angular displacement 1250 by which the rotor axis is tilted relative to the reference rotor rotational axis 1240 is greater than an occlusion detection threshold.

In the illustrated embodiment, rotor sensing arrangement (e.g., sensing arrangement 216) includes sensing elements 1230, 1232 are capable of measuring, detecting, or otherwise sensing the relative distance between a respective rotor sensing element 1230, 1232 and the rotor 1212. For example, similar to the embodiment described above in the context of FIGS. 7-8, the rotor sensing elements 1230, 1232 may be realized as Hall effect sensors capable of producing or otherwise generating an output signal that is indicative of the magnetic field strength. In this regard, as the rotor 1212 tilts away from the reference axis 1240, the distance between a first Hall effect sensor 1230 and the rotor magnet decreases, which increases the rotor magnetic field strength at the Hall effect sensor 1230 produces a corresponding increase in a characteristic of the measurement output signal produced by the Hall effect sensor 1230. Conversely, as the rotor 1212 tilts away from the reference axis 1240, the distance between the second Hall effect sensor 1232 and the rotor magnet increases, which decreases the rotor magnetic field strength at the second Hall effect sensor 1232 produces a corresponding decrease in a characteristic of the measurement output signal produced by the second Hall effect sensor 1232. Accordingly, based on the measurement signals output by the Hall effect sensors 1230, 1232, a measured amount of tilt or angular displacement 1250 for the rotor axis relative to the reference rotor axis 1240 may be calculated or otherwise determined (e.g., by the motor control module 212). When the measured tilt angle is greater than an occlusion detection threshold angle, the motor control module may identify presence of an occlusion condition and initiate one or more remedial actions in a similar manner as described above. In a similar manner as described above, one or more test actuation processes may be performed prior to the next drive cycle to confirm validity of the occlusion condition detected by the rotor axis tilting without delivering fluid to the patient (e.g., by applying a limited amount of power and observing the amount of rotor axis tilting that occurs for that reference amount of input power).

PWM Detection Techniques

As described in greater detail in U.S. Pat. No. 8,603,027, which is incorporated by reference herein, in some embodiments, the actuator driver module 214 may include or incorporate a pulse-width modulation (PWM) module configured to generate a pulse-width modulated voltage output applied to the actuator 232 via the driver module 214. In this regard, based on a duty cycle setting, the actuator driver module 214 generates or otherwise applies a pulse-width modulated voltage output to the actuator 232 that oscillates between the supply voltage provided by the energy source 218 and a ground or reference) voltage over a time interval (e.g., the PWM period), where the pulse-width modulated voltage output is equal to the supply voltage for a percentage of the time interval corresponding to the duty cycle setting. As described in U.S. Pat. No. 8,603,027, the duty cycle setting may be dynamically adjusted by the actuator control module 212 during a drive cycle to be a minimum duty cycle capable of producing actuation of the actuator 232 to thereby minimize power consumption by the actuator 232. In this regard, in response to an occlusion condition, the duty cycle setting is incrementally increased to increase the amount of torque generated by the actuator 232 to displace the plunger 217.

In one embodiment, the actuator control module 212 continually analyzes the duty cycle setting to detect or otherwise identify an occlusion condition based on the duty cycle setting. The actuator control module 212 may support or otherwise implement an average filter or mean filter that calculates or otherwise determines the average or mean duty cycle setting utilized during a preceding drive cycle. The actuator control module 212 detects or otherwise identifies an occlusion condition based on an increase in the average duty cycle setting relative to a threshold. In this regard, in one or more embodiments, the occlusion detection threshold is realized as a moving average of the average duty cycle settings across preceding drive cycles. For example, the actuator control module 212 may support or otherwise implement a moving average filter that calculates or otherwise determines a moving average of the average duty cycle setting for a preceding sequence of drive cycles. In one embodiment, the actuator control module 212 calculates or otherwise determines a moving average of the average duty cycle settings for the six preceding drive cycles. When the average duty cycle setting for the most recent drive cycle is greater than the moving average duty cycle setting across the preceding drive cycles by more than an occlusion detection threshold, the actuator control module 212 initiates one or more remedial actions as described above. In one or more embodiments, the actuator control module 212 dynamically determines the occlusion detection threshold as a percentage of the moving average duty cycle value. For example, an occlusion condition may be detected when the average duty cycle setting for the most recent drive cycle is greater than the moving average duty cycle value by at least 10% of the moving average duty cycle value.

Again, it should be noted that PWM-based occlusion detection may be implemented in connection with one or more other occlusion detection processes 300, 600, 900, 1000, 1100 described above. For example, when the PWM duty cycle setting is indicative of an occlusion condition, the control module 212 may initiate the test actuation detection process 900 to confirm validity of the occlusion condition detected based on the PWM duty cycle setting. Additionally, or alternatively, the control module 212 may initiate the acceleration detection process 1000 in connection with rewinding the actuator 232 to confirm validity of the occlusion condition detected based on the PWM duty cycle setting. In this regard, any number of the occlusion detection techniques may be implemented or combined in any number of different potential manners, and the subject matter described herein is not limited to any particular combination or hierarchical relationship of detection techniques.

For the sake of brevity, conventional techniques related to motors and related actuation systems and controls, motor sensors and/or sensing arrangements, device packaging, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. Thus, although various drawing figures may depict direct electrical connections between components, alternative embodiments may employ intervening circuit elements and/or components while functioning in a substantially similar manner.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of detecting an occlusion in a fluid path, the method comprising:
   operating, by a control module of an infusion device, a driver module to provide energy to an actuation arrangement to achieve a commanded actuation state, wherein the actuation arrangement is coupled to a plunger configured to deliver fluid via the fluid path;

ceasing, by the control module, providing of the energy to the actuation arrangement after the actuation arrangement achieved the commanded actuation state;

subsequent to the actuation arrangement achieving the commanded actuation state, obtaining, by the control module, a measured actuation state of the actuation arrangement via a sensing arrangement, the measured actuation state being a state of the actuation arrangement in which the actuation arrangement moved in a direction reverse to a direction in which the actuation arrangement moved to achieve the commanded actuation state;

determining an acceleration of the actuation arrangement or the plunger for a drive cycle based at least in part on the measured actuation state; and detecting, by the control module, an occlusion condition based on a difference between the determined acceleration and a reference acceleration for achieving the commanded actuation state and a relationship between the commanded actuation state and the measured actuation state.

2. The method of claim 1, wherein detecting the occlusion condition comprises detecting the occlusion condition when a difference between the commanded actuation state and the measured actuation state is greater than an occlusion detection threshold.

3. The method of claim 1, wherein:
operating the driver module comprises operating the driver module to provide current flow to the actuation arrangement to achieve the commanded actuation state for a first drive cycle;
obtaining the measured actuation state comprises obtaining the measured actuation state prior to operating the driver module for a subsequent drive cycle; and
determining the acceleration for the drive cycle comprises determining the acceleration for the subsequent drive cycle.

4. The method of claim 1, wherein:
the actuation arrangement comprises a motor having a rotor coupled to the plunger;
the sensing arrangement comprises a rotor sensing arrangement;
the commanded actuation state comprises a commanded rotor position; and
the measured actuation state comprises a measured rotor position.

5. The method of claim 1, further comprising:
identifying an initial resting actuation state via the sensing arrangement prior to providing a reference amount of input power to the actuation arrangement; and
determining the commanded actuation state based on the initial resting actuation state and the reference amount of input power, wherein:
operating the driver module comprises operating the driver module to provide the reference amount of input power to the actuation arrangement;
obtaining the measured actuation state of the actuation arrangement comprises obtaining the measured actuation state resulting from the reference amount of input power; and
detecting the occlusion condition comprises detecting the occlusion condition when a difference between the commanded actuation state and the measured actuation state is greater than an occlusion detection threshold.

6. The method of claim 5, wherein:
the actuation arrangement comprises a motor having a rotor coupled to the plunger;
the sensing arrangement comprises a rotor sensing arrangement;
the commanded actuation state comprises an expected rotor position; and
the measured actuation state comprises a measured rotor position.

7. The method of claim 1, the actuation arrangement comprising a motor having a rotor coupled to the plunger, the method further comprising determining an expected rotor position during operation of the driver module to provide the energy to the motor to achieve a commanded rotor position, wherein:
obtaining the measured actuation state comprises obtaining a measured rotor position via a rotor sensing arrangement; and
detecting the occlusion condition comprises detecting the occlusion condition when a difference between the expected rotor position and the measured rotor position is greater than an occlusion detection threshold.

8. The method of claim 7, wherein determining the expected rotor position comprises determining the expected rotor position based on a commutation state for the motor.

9. An infusion device comprising:
an actuation arrangement coupled to a plunger to deliver fluid via a fluid path;
a driver module coupled to the actuation arrangement to selectively provide input power to the actuation arrangement;
a sensing arrangement to measure actuation of the actuation arrangement; and
a control module coupled to the driver module and the sensing arrangement to operate the driver module to:
provide the input power to the actuation arrangement to achieve a commanded actuation state;
cease providing of the input power to the actuation arrangement after the actuation arrangement achieved the commanded actuation state;
subsequent to the actuation arrangement achieving the commanded actuation state, obtain a measured actuation state of the actuation arrangement using the sensing arrangement, the measured actuation state being a state of the actuation arrangement in which the actuation arrangement moved in a direction reverse to a direction in which the actuation arrangement moved to achieve the commanded actuation state;
determine an acceleration of the actuation arrangement or the plunger for a drive cycle based at least in part on the measured actuation state; and
detect an anomalous condition based on a difference between the determined acceleration and a reference acceleration for achieving the commanded actuation state and a relationship between the commanded actuation state and the measured actuation state.

10. The infusion device of claim 9, wherein:
the actuation arrangement comprises a motor having a rotor coupled to the plunger;
the sensing arrangement comprises a rotor sensing arrangement;
the commanded actuation state comprises a commanded rotor position; and
the measured actuation state comprises a measured rotor position.

11. The infusion device of claim 10, wherein:

the anomalous condition comprises an occlusion condition with respect to the fluid path detected when a difference between the commanded rotor position and the measured rotor position is greater than an occlusion detection threshold.

12. The infusion device of claim 9, wherein:

the input power is configured to achieve a test amount of actuation;

the control module identifies an initial resting actuation state via the sensing arrangement prior to operating the driver module to provide the input power and determines the commanded actuation state based on the initial resting actuation state and the test amount of actuation; and the anomalous condition comprises an occlusion condition detected when a difference between the commanded actuation state and the measured actuation state is greater than an occlusion detection threshold.

13. The infusion device of claim 12, wherein:

the actuation arrangement comprises a motor having a rotor coupled to the plunger;

the sensing arrangement comprises a rotor sensing arrangement;

the commanded actuation state comprises an expected rotor position; and the measured actuation state comprises a measured rotor position.

14. The infusion device of claim 9, wherein:

the actuation arrangement comprises a motor having a rotor coupled to the plunger;

the sensing arrangement comprises a rotor sensing arrangement;

the measured actuation state comprises a measured rotor position;

the commanded actuation state comprises a commanded rotor position; and the control module determines an expected rotor position based on a commutation state for the motor during operation of the driver module to achieve the commanded rotor position and detects an occlusion condition with respect to the fluid path when a difference between the expected rotor position and the measured rotor position is greater than an occlusion detection threshold.

15. A method of detecting an occlusion in a fluid path associated with an infusion device, the infusion device including a motor having a rotor coupled to a plunger displaceable to deliver fluid via the fluid path, the method comprising:

operating, by a control module of the infusion device, a driver module to provide current flow to the motor to achieve a commanded rotation of the rotor;

ceasing, by the control module, providing of the current flow to the motor after the rotor achieved the commanded rotation;

subsequent to the rotor achieving the commanded rotation, obtaining, by the control module, a measured rotor position via a rotor sensing arrangement and an acceleration of the rotor for a drive cycle based at least in part on the measured rotor position, the measured rotor position being a state of the rotor in which the rotor moved in a direction reverse to a direction in which the rotor moved to achieve the commanded rotation;

detecting, by the control module, an occlusion condition based at least in part on the measured rotor position and a difference between the obtained acceleration and a reference acceleration for achieving the commanded rotation; and initiating, by the control module, a remedial action in response to detecting the occlusion condition.

16. The method of claim 15, further comprising determining, by the control module, an expected rotor position based at least in part on the commanded rotation, wherein detecting the occlusion condition comprises detecting the occlusion condition when a difference between the expected rotor position and the measured rotor position exceeds an occlusion detection threshold.

\* \* \* \* \*